United States Patent
D'Souza et al.

(10) Patent No.: US 9,971,848 B2
(45) Date of Patent: May 15, 2018

(54) RICH FORMATTING OF ANNOTATED CLINICAL DOCUMENTATION, AND RELATED METHODS AND APPARATUS

(71) Applicant: Nuance Communications, Inc., Burlington, MA (US)

(72) Inventors: Howard D'Souza, Chantilly, VA (US); Gregory Reiser, Ashburn, VA (US); Debjani Sarkar, Herndon, VA (US)

(73) Assignee: Nuance Communications, Inc., Burlington, MA (US)

( * ) Notice: Subject to any disclaimer, the term of this patent is extended or adjusted under 35 U.S.C. 154(b) by 455 days.

(21) Appl. No.: 14/296,295

(22) Filed: Jun. 4, 2014

(65) Prior Publication Data
US 2015/0356198 A1    Dec. 10, 2015

(51) Int. Cl.
| | | |
|---|---|---|
| G06F 17/30 | (2006.01) | |
| G06F 19/00 | (2018.01) | |
| G06F 17/24 | (2006.01) | |
| G06F 17/22 | (2006.01) | |
| G06F 17/27 | (2006.01) | |

(52) U.S. Cl.
CPC .... *G06F 17/30914* (2013.01); *G06F 17/2247* (2013.01); *G06F 17/241* (2013.01); *G06F 17/245* (2013.01); *G06F 17/2785* (2013.01); *G06F 19/322* (2013.01); *G06F 19/328* (2013.01); *G06F 19/345* (2013.01)

(58) Field of Classification Search
CPC . G06F 19/322; G06F 17/2747; G06F 17/2785
See application file for complete search history.

(56) References Cited

U.S. PATENT DOCUMENTS

| | | |
|---|---|---|
| 6,292,771 B1 | 9/2001 | Haug et al. |
| 6,915,254 B1 | 7/2005 | Heinze et al. |
| 7,493,253 B1 | 2/2009 | Ceusters et al. |
| 8,694,335 B2 | 4/2014 | Yegnanarayanan |
| 8,756,079 B2 | 6/2014 | Yegnanarayanan |

(Continued)

FOREIGN PATENT DOCUMENTS

| | | |
|---|---|---|
| DE | 102007021284 A1 | 11/2008 |
| EP | 1 361 522 A2 | 11/2003 |

(Continued)

OTHER PUBLICATIONS

U.S. Appl. No. 14/296,214, filed Jun. 4, 2014, Spitznagel et al.

(Continued)

*Primary Examiner* — Sheetal R Paulson
(74) *Attorney, Agent, or Firm* — Wolf, Greenfield & Sacks, P.C.

(57) ABSTRACT

Systems and methods for producing and presenting annotations of clinical documents in a rich format are described, for instance for use with medical billing procedures. An initial XHTML document documenting a medical patient encounter and having rich formatting is used to generate a plain text document. A clinical language understanding system generates annotations, such as medical codes, which are used to annotate the XHTML document. The annotated XHTML document is then presented to a user, thus displaying for the user the annotations while retaining the rich formatting of the initial XHTML document.

20 Claims, 22 Drawing Sheets

(56) References Cited

U.S. PATENT DOCUMENTS

| | | | |
|---|---|---|---|
| 2004/0044952 A1* | 3/2004 | Jiang | G06F 17/30616 715/256 |
| 2004/0073458 A1 | 4/2004 | Jensen | |
| 2004/0220831 A1 | 11/2004 | Fabricant | |
| 2005/0228815 A1 | 10/2005 | Carus et al. | |
| 2006/0190300 A1 | 8/2006 | Drucker et al. | |
| 2007/0088564 A1 | 4/2007 | March et al. | |
| 2008/0004505 A1 | 1/2008 | Kapit et al. | |
| 2008/0147436 A1 | 6/2008 | Ohlsson | |
| 2008/0270120 A1 | 10/2008 | Pestian et al. | |
| 2010/0023319 A1 | 1/2010 | Bikel et al. | |
| 2010/0161316 A1 | 6/2010 | Haug | |
| 2010/0250236 A1 | 9/2010 | Jagannathan et al. | |
| 2012/0078763 A1 | 3/2012 | Koll et al. | |
| 2012/0089629 A1 | 4/2012 | Koll et al. | |
| 2012/0109641 A1 | 5/2012 | Boone et al. | |
| 2012/0215559 A1 | 8/2012 | Flanagan et al. | |
| 2012/0245961 A1 | 9/2012 | Yegnanarayanan | |
| 2013/0035961 A1 | 2/2013 | Yegnanarayanan | |
| 2013/0080187 A1 | 3/2013 | Bacon et al. | |
| 2013/0246098 A1 | 9/2013 | Habboush et al. | |
| 2013/0297347 A1 | 11/2013 | Cardoza et al. | |
| 2013/0297348 A1 | 11/2013 | Cardoza et al. | |
| 2014/0164023 A1 | 6/2014 | Yegnanarayanan | |
| 2014/0372147 A1 | 12/2014 | White | |
| 2015/0356057 A1 | 12/2015 | Subramanian et al. | |
| 2015/0356246 A1 | 12/2015 | D'Souza et al. | |
| 2015/0356260 A1 | 12/2015 | D'Souza et al. | |
| 2015/0356646 A1 | 12/2015 | Spitznagel et al. | |
| 2015/0356647 A1 | 12/2015 | Reiser et al. | |
| 2016/0012186 A1 | 1/2016 | Zasowski et al. | |
| 2016/0085743 A1* | 3/2016 | Haley | G06F 17/28 704/9 |

FOREIGN PATENT DOCUMENTS

| | | |
|---|---|---|
| WO | WO 2013/133891 A1 | 9/2013 |
| WO | WO 2015/084615 A1 | 6/2015 |

OTHER PUBLICATIONS

U.S. Appl. No. 14/296,249, filed Jun. 4, 2014, Subramanian et al.
U.S. Appl. No. 14/296,256, filed Jun. 4, 2014, D'Souza et al.
U.S. Appl. No. 14/296,274, filed Jun. 4, 2014, D'Souza et al.
U.S. Appl. No. 14/296,303, filed Jun. 4, 2014, Reiser et al.
Cimiano et al., "Learning concept hierarchies from text with a guided hierarchical clustering algorithm," In C. Biemann and G. Paas (eds.), Proceedings of the ICML 2005 Workshop on Learning and Extending Lexical Ontologies with Machine Learning Methods, Bonn, Germany, (2005).
Fan et al., "PRISMATIC: Inducing Knowledge from a Large Scale Lexicalized Relation Resource," Proceedings of the NAACL HLT 2010 First International Workshop on Formalisms and Methodology for Learning by Reading, pp. 122-127, Los Angeles, California, Jun. 2010.
Florian et al., "A Statistical Model for Multilingual Entity Detection and Tracking," Proceedings of the Human Language Technologies Conference 2004 (HLT-NAACL'04), (2004).
Gomez-Perez et al., "An overview of methods and tools for ontology learning from texts," Knowledge Engineering Review 19:3 p. 187-212, 2004.
Salton et al., "A Vector Space Model for Automatic Indexing," Communications of the ACM, vol. 18, No. 11, Nov. 1975.
Welty et al., "Large Scale Relation Detection," Proceedings of the NAACL HLT 2010 First International Workshop on Formalisms and Methodology for Learning by Reading, pp. 24-33, Los Angeles, California, Jun. 2010.
International Search Report and Written Opinion for International Application No. PCT/US2015/033642 dated Sep. 9, 2015.
International Search Report and Written Opinion for International Application No. PCT/US2015/033130 dated Aug. 6, 2015.
International Search Report and Written Opinion for International Application No. PCT/US2015/033648 dated Aug. 11, 2015.

* cited by examiner

Patient Name [John Doe] Sex [M] Creation Date [01-18-2011]
Document Type [Discharge Summary]

○ Chief complaint: Patient is presenting chest pain and shortness of breath.

Medical history: The patient is hypertensive. He is also obese.

Social history: He smokes one pack per day. Drinks occasionally.

⊟ Problems(:)
Add Fact | Name | Status |

⊟ Medications(0)
Add Fact | Name | Status | Schedules |

⊟ Allergies(0)
Add Fact | Name | Type | Status | Substance | Reactions |

⊟ Social History (:)
Add Alcohol Fact | Add Tobacco Fact

[Process] [Cancel]

FIG. 2

| Patient Name | John Doe | Sex | M | | |
|---|---|---|---|---|---|
| Document Type | Discharge Summary | | Creation Date | 01-18-2011 | |

Problems  Medications  Allergies  Social History  Procedures  Vital Signs      Hide All

Chief complaint: Patient is presenting chest pain and shortness of breath.

Medical history: The patient is hypertensive. He is also obese.

Social history: He smokes one pack per day. Drinks occasionally.

☐ Problems(4) — 310

Add Fact

| | Name | Status |
|---|---|---|
| x | Unspecified Chest Pain | active |
| x | Shortness of Breath | active |
| x | Unspecified Essential Hypertension | history |
| x | Obesity Unspecified | history |

☐ Medications(1) — 320

Add Fact

| | Name | Status | Type | Schedules |
|---|---|---|---|---|
| x | | | | None |

☐ Allergies(0) — 330

Add Fact

| | Name | Type | Status |
|---|---|---|---|

[Save] [Dictate] [Complete] [Cancel]

Code List

| Diagnosis | Procedure | | |
|---|---|---|---|
| ICD9 | Description | | POA |
| ✓ 518.81 | Acute Respiratory Failure | | |
| ○ 287.5 | Thrombocytopenia NOS | | |
| ○ 338.4 | Chronic Pain Syndrome | | |
| ○ 571.5 | Cirrhosis of Liver w/o Alcohol | | |
| ○ 303.90 | Alcohol Dependence NEC/NOS | | |
| ○ 571.2 | Alcoholic Cirrhosis of Liver | | |
| ○ 428.0 | Congestive Heart Failure, Unspec | | |
| ○ 482.9 | Bacterial Pneumonia NOS | | |

Discharge Summary 6/18/2014

HISTORY OF PRESENT ILLNESS/ HOSPTIAL COURSE:

The patient is a 63-year old male with a history of multiple medical problems. He was originally admitted on June 13 when he was found unresponsive at home. Left heart catheterization showed normal coronaries, and no pulmonary embolism appreciated on pulmonary angiogram. Bilateral infiltrative changes suggested pneumonia. Patient was treated for that and sent to rehab unit. He developed respiratory distress and was readmitted to the hospital with hypercapnic respiratory failure. He was intubated and put into the ICU. The [Linked to 518.81] today. No acute symptoms. He denies any chest pain or shortness of breath. No fevers or chills.

Document List

- History & Physical
  - 6/13/2014
- Discharge Summary
  - 6/18/2014
- Emergency Room Record
  - 6/13/2014
- Consultation
  - 6/16/2014
- Progress Notes
  - 6/17/2014
- Operative Report
  - 6/13/2014

Submit

Document List (710)
- History & Physical
  - 6/13/2014
  - 6/15/2014
- Discharge Summary — 712
  - 6/18/2014
- Emergency Room Record
  - 6/15/2014
- Consultation
  - 6/16/2014
- Progress Notes
  - 6/17/2014
- Operative Report
  - 6/13/2014

Submit — 750

Discharge Summary 6/18/2014 (720)

HISTORY OF PRESENT ILLNESS/
HOSPTIAL COURSE:
The patient is a 63-year old male with a history of multiple medical problems. He was originally admitted on June 13 when he was found unresponsive at home. Left heart catheterization showed normal coronaries, and no pulmonary embolism appreciated on pulmonary angiogram. Bilateral infiltrative changes suggested pneumonia. Patient was treated for that and sent to rehab unit. He developed respiratory distress and was readmitted to the hospital with hypercapnic respiratory failure. He was intubated and put into the ICU. The patient is doing well today. No acute symptoms. He denies any chest pain or shortness of breath. No fevers or chills.

Code List (730) — 740

| | Diagnosis | Procedure | | |
|---|---|---|---|---|
| | ICD9 | Description | | POA |
| ☑ | 518.81 | Acute Respiratory Failure | | |
| ○ | 287.5 | Thrombocytopenia | | |
| ○ | 338 | ▷ Show Highlights | | |
| ○ | 571 | Accept | | |
| ○ | 303 | Reject | nce | |
| | | Replace | | |
| | | Link Text | | |
| | | Unlink Text | | |
| | | NEC/NOS | | |
| ○ | 571.2 | Alcoholic Cirrhosis of Liver | | |
| ○ | 428.0 | Congestive Heart Failure, Unspec | | |
| ○ | 482.9 | Bacterial Pneumonia NOS | | |

Document List 710
- History & Physical
  - 6/13/2014
  - 6/15/2014
- Discharge Summary 712
  - 6/18/2014
- Emergency Room Record
  - 6/16/2014
- Consultation
  - 6/16/2014
- Progress Notes
  - 6/17/2014
- Operative Report
  - 6/13/2014

Submit 750

Discharge Summary 6/18/2014 — 720

DISCHARGE DIAGNOSES:
1. Acute hypercapnic respiratory failure.
2. Thrombocytopenia — 726
3. Chronic pain syndrome.
4. History of liver cirrhosis.
5. Alcoholism.
6. Congestive heart failure (CHF).
7. History of multilobular pseudomonas pneumonia in sacral wounds with general deconditioning, weakness and fatigue.

HISTORY OF PRESENT ILLNESS/ HOSPITAL COURSE
The patient is a 63-year old male with a history of multiple medical problems. He was originally admitted on June 13 when he was found Code List 730 — 740

| Diagnosis | Procedure |

| | ICD9 | Description | POA |
|---|---|---|---|
| ⊘ | 518.81 | Acute Respiratory Failure | |
| ○ | 287.5 | Thrombocytopenia NOS | /// |
| ○ | 338.4 | Chronic Pain Syndrome | |
| ○ | 571.5 | Cirrhosis of Liver w/o Alcohol | |
| ○ | 303.90 | Alcohol Dependence NEC NOS | |
| ○ | 571.2 | Alcoholic Cirrhosis of Liver | |
| ○ | 428.0 | Congestive Heart Failure, Unspec | |
| ○ | 482.9 | Bacterial Pneumonia NOS | |

700

Submit — 750

Document List — 710
- History & Physical
  - 6/13/2014
  - 6/15/2014
- Discharge Summary — 712
  - 6/18/2014
- Emergency Room Record
  - 6/13/2014
- Consultation
  - 6/16/2014
- Progress Notes
  - 6/17/2014
- Operative Report
  - 6/13/2014

720

Discharge Summary 6/18/2014

DISCHARGE DIAGNOSES:
1. Acute hypercapnic respiratory failure.
2. Thrombocytopenia.
3. Chronic pain syndrome.
4. History of liver cirrhosis.
5. Alcoholism.
6. Congestive heart failure (CHF)
7. History of multilobular pseudomonas pneumonia in sacral wounds with general deconditioning, weakness and fatigue.

HISTORY OF PRESENT ILLNESS/ HOSPITAL COURSE

The patient is a 63-year old male with a history of multiple medical problems. He was originally admitted on June 13 when he was found

Code List — 730, 740

| Diagnosis | Procedure | | |
|---|---|---|---|
| | ICD9 | Description | POA |
| ⊘ | 518.81 | Acute Respiratory Failure | |
| ⊘ | 287.5 | Thrombocytopenia NOS | |
| ⊘ | 338.4 | Chronic Pain Syndrome | |
| ⊘ | 571.5 | Cirrhosis of Liver w/o Alcohol | |
| ⊘ | 303.90 | Alcohol Dependence NEC/NOS | |
| ⊘ | 571.2 | Alcoholic Cirrhosis of Liver | |
| ⊕ | 428.0 | Congestive Heart Failure, Unspec | |
| ⊕ | 482.1 | Pneumonia due to Pseudomonas | |
| ⊕ | 041.7 | Pseudomonas Infection Site NOS | |

Document List — 710
- History & Physical
  - 6/13/2014
  - 6/15/2014
- Discharge Summary — 712
  - 6/18/2014
- Emergency Room Record
  - 6/13/2014
- Consultation
- Progress Notes
  - 6/17/2014
- Operative Report
  - 6/13/2014

Submit — 750

720

Discharge Summary 6/18/2014
DISCHARGE DIAGNOSES:
1. Acute hypercapnic respiratory failure.
2. Thrombocytopenia.
3. Chronic pain syndrome.
4. History of liver cirrhosis.
5. Alcoholism.
6. Congestive heart failure (CH
7. History of multilobular pseudomonas pneumonia in sacral wounds with general deconditioning, weakness and fatigue.

HISTORY OF PRESENT ILLNESS/HOSPITAL COURSE

The patient is a 63-year old male with a history of multiple medical problems. He was originally admitted on June 13 when he was found

730

Code List — 740

| Diagnosis | Procedure |

| | ICD9 | Description | POA |
|---|---|---|---|
| ⊘ | 518.81 | Acute Respiratory Failure | |
| ⊘ | 287.5 | Thrombocytopenia NOS | |
| | 4 | Chronic Pain Syndrome | |
| | 5 | Cirrhosis of Liver | |
| ⊕ | 57 | | |
| ⊕ | 42 | | |
| ⊕ | 482.1 | Pneumonia due to Pseudomonas | |
| ⊕ | 041.7 | Pseudomonas Infection Site NOS | |

Popup menu:
- Incorrect Code
- More specific code needed
- Partial Code
- Negated Code
- Not Billable
- Payor Specific Show Highlights
Accept
Rejected Reason
Replace
Link Text
Unlink Text

700

```
<ccav ccavICD10Version="6" ccavVersion="5" visitId="8716e5f5-e532-402c-b242-16fae0492cfa">
  <documentCodes>
  - <documentCode cluDocumentId="10407" annotatedId="4418" codeId="V76.51">
      <codingSystem type="ICD9"/>
      <description>SPECIAL SCREENING FOR MALIGNANT NEOPLASMS COLON</description>
      <confidenceLevel>30.0</confidenceLevel>
      <order>4</order>
      <systemStatus>SUGGESTED</systemStatus>
    - <tokens>
      - <token cluDocumentId="10407" annotatedId="18">
          <tokenOffsets end="29" start="18"/>
          <isDeleted>false</isDeleted>
        </token>
      - <token cluDocumentId="10407" annotatedId="114">
          <tokenOffsets end="119" start="114"/>
          <isDeleted>false</isDeleted>
        </token>
      - <token cluDocumentId="10407" annotatedId="120">
          <tokenOffsets end="126" start="120"/>
          <isDeleted>false</isDeleted>
        </token>
```

FIG. 12B

RICH FORMATTING OF ANNOTATED CLINICAL DOCUMENTATION, AND RELATED METHODS AND APPARATUS

BACKGROUND

Medical documentation is an important process in the healthcare industry. Most healthcare institutions maintain a longitudinal medical record (e.g., spanning multiple observations or treatments over time) for each of their patients, documenting, for example, the patient's history, encounters with clinical staff within the institution, treatment received, and/or plans for future treatment. Such documentation facilitates maintaining continuity of care for the patient across multiple encounters with various clinicians over time. In addition, when an institution's medical records for large numbers of patients are considered in the aggregate, the information contained therein can be useful for educating clinicians as to treatment efficacy and best practices, for internal auditing within the institution, for quality assurance, etc.

Historically, each patient's medical record was maintained as a physical paper folder, often referred to as a "medical chart", or "chart". Each patient's chart would include a stack of paper reports, such as intake forms, history and immunization records, laboratory results and clinicians' notes. Following an encounter with the patient, such as an office visit, a hospital round or a surgical procedure, the clinician conducting the encounter would provide a narrative note about the encounter to be included in the patient's chart. Such a note could include, for example, a description of the reason(s) for the patient encounter, an account of any vital signs, test results and/or other clinical data collected during the encounter, one or more diagnoses determined by the clinician from the encounter, and a description of a plan for further treatment. Often, the clinician would verbally dictate the note into an audio recording device or a telephone giving access to such a recording device, to spare the clinician the time it would take to prepare the note in written form. Later, a medical transcriptionist would listen to the audio recording and transcribe it into a text document, which would be inserted on a piece of paper into the patient's chart for later reference.

Currently, many healthcare institutions are transitioning or have transitioned from paper documentation to electronic medical record systems, in which patients' longitudinal medical information is stored in a data repository in electronic form. Besides the significant physical space savings afforded by the replacement of paper record-keeping with electronic storage methods, the use of electronic medical records also provides beneficial time savings and other opportunities to clinicians and other healthcare personnel. For example, when updating a patient's electronic medical record to reflect a current patient encounter, a clinician need only document the new information obtained from the encounter, and need not spend time entering unchanged information such as the patient's age, gender, medical history, etc. Electronic medical records can also be shared, accessed and updated by multiple different personnel from local and remote locations through suitable user interfaces and network connections, eliminating the need to retrieve and deliver paper files from a crowded file room.

Another modern trend in healthcare management is the importance of medical coding for documentation and billing purposes. In the medical coding process, documented information regarding a patient encounter, such as the patient's diagnoses and clinical procedures performed, is classified according to one or more standardized sets of codes for reporting to various entities such as payment providers (e.g., health insurance companies that reimburse clinicians for their services). In the United States, some such standardized code systems have been adopted by the federal government, which then maintains the code sets and recommends or mandates their use for billing under programs such as Medicare.

For example, the International Classification of Diseases (ICD) numerical coding standard, developed from a European standard by the World Health Organization (WHO), was adopted in the U.S. in version ICD-9-CM (Clinically Modified). It is mandated by the Health Insurance Portability and Accountability Act of 1996 (HIPAA) for use in coding patient diagnoses. The Centers for Disease Control (CDC), the National Center for Health Statistics (NCHS), and the Centers for Medicare and Medicaid Services (CMS) are the U.S. government agencies responsible for overseeing all changes and modifications to ICD-9-CM, and a new version ICD-10-CM is scheduled for adoption in 2015.

Another example of a standardized code system adopted by the U.S. government is the Current Procedural Terminology (CPT) code set, which classifies clinical procedures in five-character alphanumeric codes. The CPT code set is owned by the American Medical Association (AMA), and its use is mandated by CMS as part of the Healthcare Common Procedure Coding System (HCPCS). CPT forms HCPCS Level I, and HCPCS Level II adds codes for medical supplies, durable medical goods, non-physician healthcare services, and other healthcare services not represented in CPT. CMS maintains and distributes the HCPCS Level II codes with quarterly updates.

Conventionally, the coding of a patient encounter has been a manual process performed by a human professional, referred to as a "medical coder" or simply "coder," with expert training in medical terminology and documentation as well as the standardized code sets being used and the relevant regulations. The coder would read the available documentation from the patient encounter, such as the clinicians' narrative reports, laboratory and radiology test results, etc., and determine the appropriate codes to assign to the encounter. The coder might make use of a medical coding system, such as a software program running on suitable hardware, that would display the documents from the patient encounter for the coder to read, and allow the coder to manually input the appropriate codes into a set of fields for entry in the record. Once finalized, the set of codes entered for the patient encounter could then be sent to a payment provider, which would typically determine the level of reimbursement for the encounter according to the particular codes that were entered.

SUMMARY

One type of embodiment is directed to a method comprising: converting a medical document having rich formatting into a first XHTML document; generating a plain text document from the first XHTML document; generating one or more annotations of the plain text document by applying a natural language understanding (NLU) engine implemented on a processor to the plain text document; and creating an annotated XHTML document by applying the one or more annotations of the plain text document to a tokenized XHTML document representing the medical document.

Another type of embodiment is directed to a computer-readable storage medium having instructions that, when executed by a processor, cause performance of a method comprising: converting a medical document having rich formatting into a first XHTML document; generating a plain text document from the first XHTML document; generating one or more annotations of the plain text document by applying a natural language understanding (NLU) engine implemented on a processor to the plain text document; and creating an annotated XHTML document by applying the one or more annotations of the plain text document to a tokenized XHTML document representing the medical document.

Another type of embodiment is directed to a system, comprising a processor, and a memory coupled to the processor and storing computer-readable instructions which, when executed by the processor, cause performance of a method comprising: converting a medical document having rich formatting into a first XHTML document; generating a plain text document from the first XHTML document; generating one or more annotations of the plain text document by applying a natural language understanding (NLU) engine implemented on a processor to the plain text document; and creating an annotated XHTML document by applying the one or more annotations of the plain text document to a tokenized XHTML document representing the medical document.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2 is a screenshot illustrating an exemplary graphical user interface for review of extracted medical facts in accordance with some embodiments;

FIGS. 3A and 3B are screenshots illustrating an exemplary display of medical facts in a user interface in accordance with some embodiments;

FIG. 4 is a screenshot illustrating an exemplary display of linkage between text and a medical fact in accordance with some embodiments;

FIG. 5 is a screenshot illustrating an exemplary interface for entering a medical fact in accordance with some embodiments;

FIGS. 7A-7F are screenshots illustrating an exemplary user interface for a computer-assisted coding (CAC) system in accordance with some embodiments;

FIGS. 12A-12C illustrate non-limiting examples of documents which may be used in connection with aspects of the present application relating to annotating richly formatted content;

DETAILED DESCRIPTION

Figure 1:
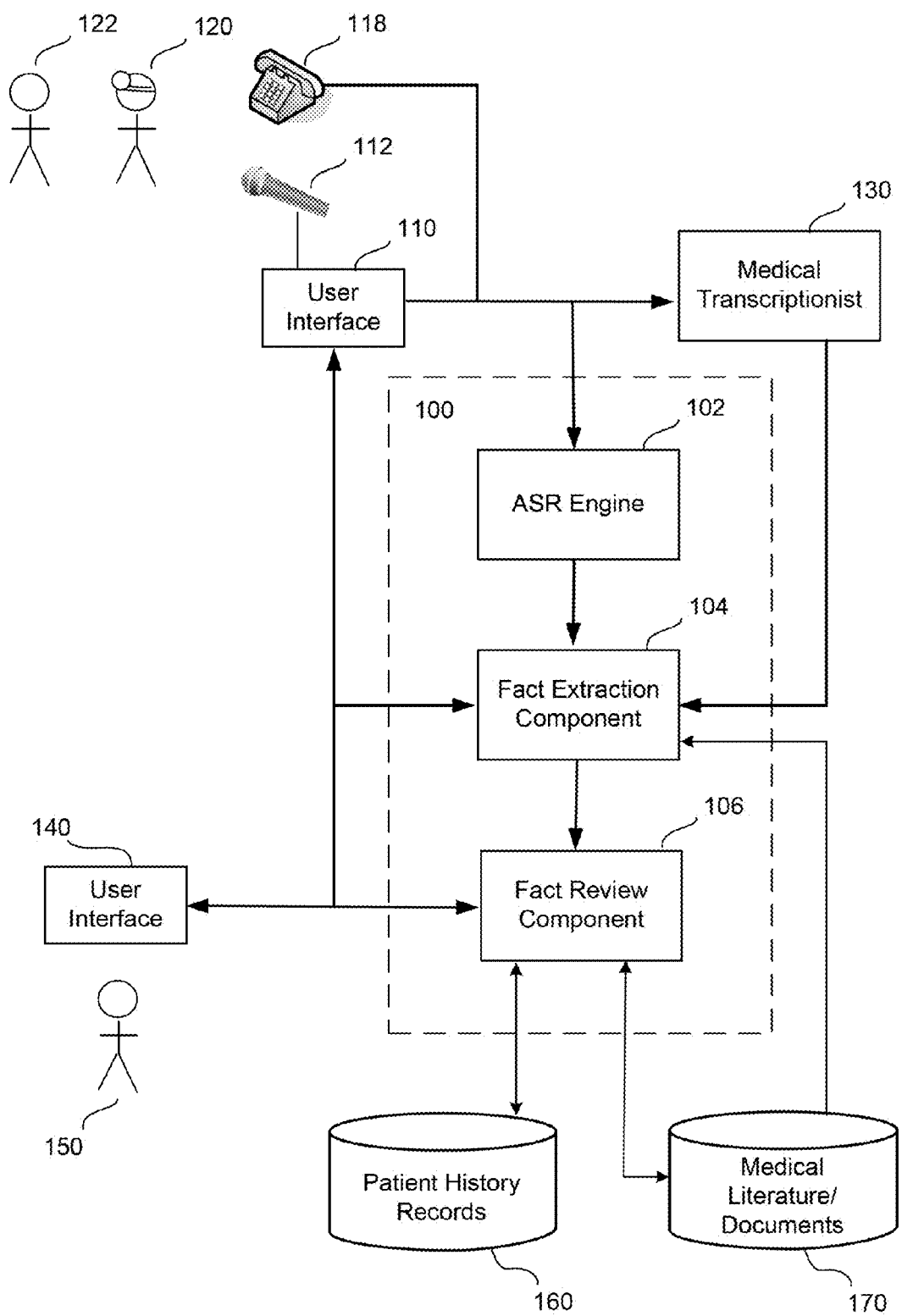
FIG. 1 is a block diagram of an exemplary operating environment for a clinical language understanding (CLU) system that may be employed in connection with some embodiments.

Aspects of the present application are directed to providing a user with annotated medical records in rich formats. In some embodiments, medical documents relating to a patient encounter are processed with a clinical language understanding (CLU) system, for instance using a natural language understanding (NLU) engine of the CLU system, which generates annotations and evidence. Examples of possible functionality of a CLU system are described below. As used herein, the term "annotation" refers to an item derived from and linked to a portion of text, such as a fact (e.g., a medical fact, one particular example of which may be a medical code such as a medical billing code), a semantic label, or other such item having a link to one or more corresponding portions of text from which it was or could be derived. The annotations generated by a CLU system can include, among other things, medically related codes for information appearing in the medical document, such as medical diagnosis codes and/or medical procedure codes, which may function as billing codes. An annotated document may then be presented to the user including the annotations (e.g., the billing codes such as diagnosis and/or procedure codes generated by the system) together with evidence supporting the annotations in rich format, allowing the user to readily discern the basis and context for the annotations. Such a configuration may provide greater information to a user than an annotated plain text document, which often omits valuable formatting information which could aid a user in evaluating the provided annotations.

According to some embodiments, presenting an annotated document in rich formatting involves conversion of a rich text document to a plain text document, generation of annotations of the plain text document, and mapping of the annotations back to a rich text document. For instance, a richly formatted medical record to be annotated (e.g., with diagnoses codes, procedure codes, or other billing codes) may be converted to an XHTML document which is structured to represent the rich formatting of the medical record. A plain text document may then be generated from the XHTML document (e.g., by extracting content from the XHTML document) and annotated, for example with codes of the types described above. A tokenized XHTML document may then be generated, and annotations and evidence may be applied to the tokenized XHTML document by an application viewer which presents the annotations to a user. In this manner, the annotations and corresponding evidence may be presented to the user with the benefit of rich formatting. In some embodiments, the annotations are applied to the XHTML document only in a transient document presented to a user (e.g., via a browser), and there is no annotated richly formatted document maintained by the system.

According to an aspect of the present application, a user may edit (e.g., add to, remove from, or revise) annotations (e.g., medical codes and evidence) associated with a richly formatted annotated document, and the information generated by such editing may be used to train a CLU system (e.g., the NLU engine of a CLU system) which generated the annotations. In some embodiments, a richly formatted annotated document may be generated as described above and presented to the user. The user may then select one or more portions of the document and edit annotations (e.g., by replacing a code associated with the portion, adding a code, removing a code, and/or linking the selected portion to one or more codes). Information about the portion(s) selected by the user and the corresponding user-added annotations may then be sent to the CLU system for training. In this manner, CLU system accuracy may be improved.

The aspects and embodiments described above, as well as additional aspects and embodiments, are described further below. While a number of inventive features for clinical documentation processes are described above, it should be appreciated that embodiments of the present invention may include any one of these features, any combination of two or more features, or all of the features, as aspects of the invention are not limited to any particular number or combination of the above-described features. The aspects of the present invention described herein can be implemented in any of numerous ways, and are not limited to any particular implementation techniques. Described below are examples of specific implementation techniques; however, it should be appreciate that these examples are provided merely for purposes of illustration, and that other implementations are possible.

Clinical Language Understanding (CLU) System

An Electronic Health Record (EHR) is an electronic medical record that generally is maintained by a specific healthcare institution and contains data documenting the care that a specific patient has received from that institution over time. Typically, an EHR is maintained as a structured data representation, such as a database with structured fields. Each piece of information stored in such an EHR is typically represented as a discrete (e.g., separate) data item occupying a field of the EHR database. For example, a 55-year old male patient named John Doe may have an EHR database record with "John Doe" stored in the patient_name field, "55" stored in the patient_age field, and "Male" stored in the patient_gender field. Data items or fields in such an EHR are structured in the sense that only a certain limited set of valid inputs is allowed for each field. For example, the patient_name field may require an alphabetic string as input, and may have a maximum length limit; the patient_age field may require a string of three numerals, and the leading numeral may have to be "0" or "1"; the patient_gender field may only allow one of two inputs, "Male" and "Female"; a patient_birth_date field may require input in a "MM/DD/YYYY" format; etc.

Typical EHRs are also structured in terms of the vocabulary they use, as medical terms are normalized to a standard set of terms utilized by the institution maintaining the EHR. The standard set of terms may be specific to the institution, or may be a more widely used standard. For example, a clinician dictating or writing a free-form note may use any of a number of different terms for the condition of a patient currently suffering from an interruption of blood supply to the heart, including "heart attack", "acute myocardial infarction", "acute MI" and "AMI". To facilitate interoperability of EHR data between various departments and users in the institution, and/or to allow identical conditions to be identified as such across patient records for data analysis, a typical EHR may use only one standardized term to represent each individual medical concept. For example, "acute myocardial infarction" may be the standard term stored in the EHR for every case of a heart attack occurring at the time of a clinical encounter. Some EHRs may represent medical terms in a data format corresponding to a coding standard, such as the International Classification of Disease (ICD) standard. For example, "acute myocardial infarction" may be represented in an EHR as "ICD-9 410", where 410 is the code number for "acute myocardial infarction" according to the ninth edition of the ICD standard.

To allow clinicians and other healthcare personnel to enter medical documentation data directly into an EHR in its discrete structured data format, many EHRs are accessed through user interfaces that make extensive use of point-and-click input methods. While some data items, such as the patient's name, may require input in (structured) textual or numeric form, many data items can be input simply through the use of a mouse or other pointing input device (e.g., a touch screen) to make selections from pre-set options in drop-down menus and/or sets of checkboxes and/or radio buttons or the like.

While some clinicians may appreciate the ability to directly enter structured data into an EHR through a point-and-click interface, many clinicians may prefer being unconstrained in what they can say and in what terms they can use in a free-form note, and many may be reluctant to take the time to learn where all the boxes and buttons are and what they all mean in an EHR user interface. In addition, many clinicians may prefer to take advantage of the time savings that can be gained by providing notes through verbal dictation, as speech can often be a faster form of data communication than typing or clicking through forms.

Accordingly, some embodiments described herein relate to techniques for enhancing the creation and use of structured electronic medical records, using techniques that enable a clinician to provide input and observations via a free-form narrative clinician's note. Some embodiments involve the automatic extraction of discrete medical facts (e.g., clinical facts), such as could be stored as discrete structured data items in an electronic medical record, from a clinician's free-form narration of a patient encounter. In this manner, free-form input may be provided, but the advantages of storage, maintenance and accessing of medical documentation data in electronic forms may be maintained. For example, the storage of a patient's medical documentation data as a collection of discrete structured data items may provide the benefits of being able to query for individual data items of interest, and being able to assemble arbitrary subsets of the patient's data items into new reports, orders, invoices, etc., in an automated and efficient manner.

Automatic extraction of medical facts (e.g., clinical facts) from a free-form narration may be performed in any suitable way using any suitable technique(s), as aspects of the present invention are not limited in this respect. In some embodiments, pre-processing may be performed on a free-form narration prior to performing automatic fact extraction, to determine the sequence of words represented by the free-form narration. Such pre-processing may also be performed in any suitable way using any suitable technique(s), as aspects of the present invention are not limited in this respect. For example, in some embodiments, the clinician may provide the free-form narration directly in textual form (e.g., using a keyboard or other text entry device), and the textual free-form narration may be automatically parsed to determine its sequence of words. In other embodiments, the clinician may provide the free-form narration in audio form as a spoken dictation, and an audio recording of the clinician's spoken dictation may be received and/or stored. The audio input may be processed in any suitable way prior to or in the process of performing fact extraction, as aspects of the invention are not limited in this respect. In some embodiments, the audio input may be processed to form a textual representation, and fact extraction may be performed on the textual representation. Such processing to produce a textual representation may be performed in any suitable way. For example, in some embodiments, the audio recording may be transcribed by a human transcriptionist, while in other embodiments, automatic speech recognition (ASR) may be performed on the audio recording to obtain a textual representation of the free-form narration provided via the clinician's dictation. Any suitable automatic speech recognition technique may be used, as aspects of the present invention are not limited in this respect. In other embodiments, speech-to-text conversion of the clinician's audio dictation may not be required, as a technique that does not involve processing the audio to produce a textual representation may be used to determine what was spoken. In one example, the sequence of words that was spoken may be determined directly from the audio recording, e.g., by comparing the audio recording to stored waveform templates to determine the sequence of words. In other examples, the clinician's speech may not be recognized as words, but may be recognized in another form such as a sequence or collection of abstract concepts. It should be appreciated that the words and/or concepts represented in the clinician's free-form narration may be represented and/or stored as data in any suitable form, including forms other than a textual representation, as aspects of the present invention are not limited in this respect.

In some embodiments, one or more medical facts (e.g., clinical facts) may be automatically extracted from the free-form narration (in audio or textual form) or from a pre-processed data representation of the free-form narration using a fact extraction component applying natural language understanding techniques, such as a natural language understanding (NLU) engine. In some embodiments, the medical facts to be extracted may be defined by a set of fact categories (also referred to herein as "fact types" or "entity types") commonly used by clinicians in documenting patient encounters. In some embodiments, a suitable set of fact categories may be defined by any of various known healthcare standards. For example, in some embodiments, the medical facts to be extracted may include facts that are required to be documented by Meaningful Use standards promulgated by the U.S. government, e.g., under 42 C.F.R. § 495, which sets forth "Objectives" specifying items of medical information to be recorded for medical patients. Such facts currently required by the Meaningful Use standards include social history facts, allergy facts, diagnostic test result facts, medication facts, problem facts, procedure facts, and vital sign facts. However, these are merely exemplary, as aspects of the invention are not limited to any particular set of fact categories. Some embodiments may not use one or more of the above-listed fact categories, and some embodiments may use any other suitable fact categories. Other non-limiting examples of suitable categories of medical facts include findings, disorders, body sites, medical devices, subdivided categories such as observable findings and measurable findings, etc. The fact extraction component may be implemented in any suitable form, as aspects of the present invention are not limited in this respect. Exemplary implementations for a fact extraction component are described in detail below.

Some embodiments described herein may make use of a clinical language understanding (CLU) system, an exemplary operating environment for which is illustrated in FIG. 1. CLU system 100, illustrated in FIG. 1, may be implemented in any suitable form, as aspects of the present invention are not limited in this respect. For example, system 100 may be implemented as a single stand-alone machine, or may be implemented by multiple distributed machines that share processing tasks in any suitable manner. System 100 may be implemented as one or more computers; an example of a suitable computer is described below. In some embodiments, system 100 may include one or more tangible, non-transitory computer-readable storage devices storing processor-executable instructions, and one or more processors that execute the processor-executable instructions to perform the functions described herein. The storage devices may be implemented as computer-readable storage media encoded with the processor-executable instructions; examples of suitable computer-readable storage media are discussed below.

As depicted, exemplary system 100 includes an ASR engine 102, a fact extraction component 104, and a fact review component 106. Each of these processing components of system 100 may be implemented in software, hardware, or a combination of software and hardware. Components implemented in software may comprise sets of processor-executable instructions that may be executed by the one or more processors of system 100 to perform the functionality described herein. Each of ASR engine 102, fact extraction component 104 and fact review component 106 may be implemented as a separate component of system 100, or any combination of these components may be integrated into a single component or a set of distributed components. In addition, any one of ASR engine 102, fact extraction component 104 and fact review component 106 may be implemented as a set of multiple software and/or hardware components. It should be understood that any such component depicted in FIG. 1 is not limited to any particular software and/or hardware implementation and/or configuration. Also, not all components of exemplary system 100 illustrated in FIG. 1 are required in all embodiments. For example, in some embodiments, a CLU system may include functionality of fact extraction component 104, which may be implemented using a natural language understanding (NLU) engine, without including ASR engine 102 and/or fact review component 106.

As illustrated in FIG. 1, user interface 110 is presented to a clinician 120, who may be a physician, a physician's aide, a nurse, or any other personnel involved in the evaluation and/or treatment of a patient 122 in a clinical setting. During the course of a clinical encounter with patient 122, or at some point thereafter, clinician 120 may wish to document the patient encounter. Such a patient encounter may include any interaction between clinician 120 and patient 122 in a clinical evaluation and/or treatment setting, including, but not limited to, an office visit, an interaction during hospital rounds, an outpatient or inpatient procedure (surgical or non-surgical), a follow-up evaluation, a visit for laboratory or radiology testing, etc. One method that clinician 120 may use to document the patient encounter may be to enter medical facts that can be ascertained from the patient encounter into user interface 110 as discrete structured data items. The set of medical facts, once entered, may be transmitted in some embodiments via any suitable communication medium or media (e.g., local and/or network connection(s) that may include wired and/or wireless connection(s)) to system 100. Specifically, in some embodiments, the set of medical facts may be received at system 100 by a fact review component 106, exemplary functions of which are described below.

Another method that may be used by clinician 120 to document the patient encounter is to provide a free-form narration of the patient encounter. In some embodiments, the narration may be free-form in the sense that clinician 120 may be unconstrained with regard to the structure and content of the narration, and may be free to provide any sequence of words, sentences, paragraphs, sections, etc., that he would like. In some embodiments, there may be no limitation on the length of the free-form narration, or the length may be limited only by the processing capabilities of the user interface into which it is entered or of the later processing components that will operate upon it. In other embodiments, the free-form narration may be constrained in length (e.g., limited to a particular number of characters).

A free-form narration of the patient encounter may be provided by clinician 120 in any of various ways. One way may be to manually enter the free-form narration in textual form into user interface 110, e.g., using a keyboard. In this respect, the one or more processors of system 100 and/or of a client device in communication with system 100 may in some embodiments be programmed to present a user interface including a text editor/word processor to clinician 120. Such a text editor/word processor may be implemented in any suitable way, as aspects of the present invention are not limited in this respect.

Another way to provide a free-form narration of the patient encounter may be to verbally speak a dictation of the patient encounter. Such a spoken dictation may be provided in any suitable way, as aspects of the present invention are not limited in this respect. As illustrated in FIG. 1, one way that clinician 120 may provide a spoken dictation of the free-form narration may be to speak the dictation into a microphone 112 providing input (e.g., via a direct wired connection, a direct wireless connection, or via a connection through an intermediate device) to user interface 110. An audio recording of the spoken dictation may then be stored in any suitable data format, and transmitted to system 100 and/or to medical transcriptionist 130. Another way that clinician 120 may provide the spoken dictation may be to speak into a telephone 118, from which an audio signal may be transmitted to be recorded at system 100, at the site of medical transcriptionist 130, or at any other suitable location. Alternatively, the audio signal may be recorded in any suitable data format at an intermediate facility, and the audio data may then be relayed to system 100 and/or to medical transcriptionist 130.

In some embodiments, medical transcriptionist 130 may receive the audio recording of the dictation provided by clinician 120, and may transcribe it into a textual representation of the free-form narration (e.g., into a text narrative). Medical transcriptionist 130 may be any human who listens to the audio dictation and writes or types what was spoken into a text document. In some embodiments, medical transcriptionist 130 may be specifically trained in the field of medical transcription, and may be well-versed in medical terminology. In some embodiments, medical transcriptionist 130 may transcribe exactly what she hears in the audio dictation, while in other embodiments, medical transcriptionist 130 may add formatting to the text transcription to comply with generally accepted medical document standards. When medical transcriptionist 130 has completed the transcription of the free-form narration into a textual representation, the resulting text narrative may in some embodiments be transmitted to system 100 or any other suitable location (e.g., to a storage location accessible to system 100). Specifically, in some embodiments the text narrative may be received from medical transcriptionist 130 by fact extraction component 104 within system 100. Exemplary functionality of fact extraction component 104 is described below.

In some other embodiments, the audio recording of the spoken dictation may be received, at system 100 or any other suitable location, by automatic speech recognition (ASR) engine 102. In some embodiments, ASR engine 102 may then process the audio recording to determine what was spoken. As discussed above, such processing may involve any suitable speech recognition technique, as aspects of the present invention are not limited in this respect. In some embodiments, the audio recording may be automatically converted to a textual representation, while in other embodiments, words identified directly from the audio recording may be represented in a data format other than text, or abstract concepts may be identified instead of words. Examples of further processing are described below with reference to a text narrative that is a textual representation of the free-form narration; however, it should be appreciated that similar processing may be performed on other representations of the free-form narration as discussed above. When a textual representation is produced, in some embodiments it may be reviewed by a human (e.g., a transcriptionist) for accuracy, while in other embodiments the output of ASR engine 102 may be accepted as accurate without human review. As discussed above, some embodiments are not limited to any particular method for transcribing audio data; an audio recording of a spoken dictation may be transcribed manually by a human transcriptionist, automatically by ASR, or semiautomatically by human editing of a draft transcription produced by ASR. Transcriptions produced by ASR engine 102 and/or by transcriptionist 130 may be encoded or otherwise represented as data in any suitable form, as aspects of the invention are not limited in this respect.

In some embodiments, ASR engine 102 may make use of a lexicon of medical terms (which may be part of, or in addition to, another more general speech recognition lexicon) while determining the sequence of words that were spoken in the free-form narration provided by clinician 120. However, aspects of the invention are not limited to the use of a lexicon, or any particular type of lexicon, for ASR. When used, the medical lexicon in some embodiments may be linked to a knowledge representation model such as a clinical language understanding ontology utilized by fact extraction component 104, such that ASR engine 102 might produce a text narrative containing terms in a form understandable to fact extraction component 104. In some embodiments, a more general speech recognition lexicon might also be shared between ASR engine 102 and fact extraction component 104. However, in other embodiments, ASR engine 102 may not have any lexicon developed to be in common with fact extraction component 104. In some embodiments, a lexicon used by ASR engine 102 may be linked to a different type of medical knowledge representation model, such as one not designed or used for language understanding. It should be appreciated that any lexicon used by ASR engine 102 and/or fact extraction component 104 may be implemented and/or represented as data in any suitable way, as aspects of the invention are not limited in this respect.

In some embodiments, a text narrative, whether produced by ASR engine 102 (and optionally verified or not by a human), produced by medical transcriptionist 130, directly entered in textual form through user interface 110, or produced in any other way, may be re-formatted in one or more ways before being received by fact extraction component 104. Such re-formatting may be performed by ASR engine 102, by a component of fact extraction component 104, by a combination of ASR engine 102 and fact extraction component 104, or by any other suitable software and/or hardware component. In some embodiments, the re-formatting may be performed in a way known to facilitate fact extraction, and may be performed for the purpose of facilitating the extraction of clinical facts from the text narrative by fact extraction component 104. For example, in some embodiments, processing to perform fact extraction may be improved if sentence boundaries in the text narrative are accurate. Accordingly, in some embodiments, the text narrative may be re-formatted prior to fact extraction to add, remove or correct one or more sentence boundaries within the text narrative. In some embodiments, this may involve altering the punctuation in at least one location within the text narrative. In another example, fact extraction may be improved if the text narrative is organized into sections with headings, and thus the re-formatting may include determining one or more section boundaries in the text narrative and adding, removing or correcting one or more corresponding section headings. In some embodiments, the re-formatting may include normalizing one or more section headings (which may have been present in the original text narrative and/or added or corrected as part of the re-formatting) according to a standard for the healthcare institution corresponding to the patient encounter (which may be an institution-specific standard or a more general standard for section headings in clinical documents). In some embodiments, a user (such as clinician 120, medical transcriptionist 130, or another user) may be prompted to approve the re-formatted text.

In some embodiments, either an original or a re-formatted text narrative may be received by fact extraction component 104, which may perform processing to extract one or more medical facts (e.g., clinical facts) from the text narrative. The text narrative may be received from ASR engine 102, from medical transcriptionist 130, directly from clinician 120 via user interface 110, or in any other suitable way. Any suitable technique(s) for extracting facts from the text narrative may be used, as aspects of the present invention are not limited in this respect. Exemplary techniques for medical fact extraction are described below.

In some embodiments, a fact extraction component may be implemented using techniques such as those described in U.S. Pat. No. 7,493,253, entitled "Conceptual World Representation Natural Language Understanding System and Method." U.S. Pat. No. 7,493,253 is incorporated herein by reference in its entirety. Such a fact extraction component may make use of a formal ontology linked to a lexicon of clinical terms. The formal ontology may be implemented as a relational database, or in any other suitable form, and may represent semantic concepts relevant to the medical domain, as well as linguistic concepts related to ways the semantic concepts may be expressed in natural language.

In some embodiments, concepts in a formal ontology used by a fact extraction component may be linked to a lexicon of medical terms and/or codes, such that each medical term and each code is linked to at least one concept in the formal ontology. In some embodiments, the lexicon may include the standard medical terms and/or codes used by the institution in which the fact extraction component is applied. For example, the standard medical terms and/or codes used by an EHR maintained by the institution may be included in the lexicon linked to the fact extraction component's formal ontology. In some embodiments, the lexicon may also include additional medical terms used by the various clinicians within the institution, and/or used by clinicians generally, when describing medical issues in a free-form narration. Such additional medical terms may be linked, along with their corresponding standard medical terms, to the appropriate shared concepts within the formal ontology. For example, the standard term "acute myocardial infarction" as well as other corresponding terms such as "heart attack", "acute MI" and "AMI" may all be linked to the same abstract concept in the formal ontology—a concept representing an interruption of blood supply to the heart. Such linkage of multiple medical terms to the same abstract concept in some embodiments may relieve the clinician of the burden of ensuring that only standard medical terms preferred by the institution appear in the free-form narration. For example, in some embodiments, a clinician may be free to use the abbreviation "AMI" or the colloquial "heart attack" in his free-form narration, and the shared concept linkage may allow the fact extraction component to nevertheless automatically extract a fact corresponding to "acute myocardial infarction".

In some embodiments, a formal ontology used by a fact extraction component may also represent various types of relationships between the concepts represented. One type of relationship between two concepts may be a parent-child relationship, in which the child concept is a more specific version of the parent concept. More formally, in a parent-child relationship, the child concept inherits all necessary properties of the parent concept, while the child concept may have necessary properties that are not shared by the parent concept. For example, "heart failure" may be a parent concept, and "congestive heart failure" may be a child concept of "heart failure." In some embodiments, any other type(s) of relationship useful to the process of medical documentation may also be represented in the formal ontology. For example, one type of relationship may be a symptom relationship. In one example of a symptom relationship, a concept linked to the term "chest pain" may have a relationship of "is-symptom-of" to the concept linked to the term "heart attack". Other types of relationships may include complication relationships, comorbidity relationships, interaction relationships (e.g., among medications), and many others. Any number and type(s) of concept relationships may be included in such a formal ontology, as aspects of the present invention are not limited in this respect.

In some embodiments, automatic extraction of medical facts from a clinician's free-form narration may involve parsing the free-form narration to identify medical terms that are represented in the lexicon of the fact extraction component. Concepts in the formal ontology linked to the medical terms that appear in the free-form narration may then be identified, and concept relationships in the formal ontology may be traced to identify further relevant concepts. Through these relationships, as well as the linguistic knowledge represented in the formal ontology, one or more medical facts may be extracted. For example, if the free-form narration includes the medical term "hypertension" and the linguistic context relates to the patient's past, the fact extraction component may automatically extract a fact indicating that the patient has a history of hypertension. On the other hand, if the free-form narration includes the medical term "hypertension" in a sentence about the patient's mother, the fact extraction component may automatically extract a fact indicating that the patient has a family history of hypertension. In some embodiments, relationships between concepts in the formal ontology may also allow the fact extraction component to automatically extract facts containing medical terms that were not explicitly included in the free-form narration. For example, the medical term "meningitis" can also be described as inflammation in the brain. If the free-form narration includes the terms "inflammation" and "brain" in proximity to each other, then relationships in the formal ontology between concepts linked to the terms "inflammation", "brain" and "meningitis" may allow the fact extraction component to automatically extract a fact corresponding to "meningitis", despite the fact that the term "meningitis" was not stated in the free-form narration.

It should be appreciated that the foregoing descriptions are provided by way of example only, and that any suitable technique(s) for extracting a set of one or more medical facts from a free-form narration may be used, as aspects of the present invention are not limited to any particular fact extraction technique. For instance, it should be appreciated that fact extraction component 104 is not limited to the use of an ontology, as other forms of knowledge representation models, including statistical models and/or rule-based models, may also be used. The knowledge representation model may also be represented as data in any suitable format, and may be stored in any suitable location, such as in a storage medium of system 100 accessible by fact extraction component 104, as aspects of the invention are not limited in this respect. In addition, a knowledge representation model such as an ontology used by fact extraction component 104 may be constructed in any suitable way, as aspects of the invention are not limited in this respect.

For instance, in some embodiments a knowledge representation model may be constructed manually by one or more human developers with access to expert knowledge about medical facts, diagnoses, problems, potential complications, comorbidities, appropriate observations and/or clinical findings, and/or any other relevant information. In other embodiments, a knowledge representation model may be generated automatically, for example through statistical analysis of past medical reports documenting patient encounters, of medical literature and/or of other medical documents. Thus, in some embodiments, fact extraction component 104 may have access to a data set 170 of medical literature and/or other documents such as past patient encounter reports. In some embodiments, past reports and/or other text documents may be marked up (e.g., by a human) with labels indicating the nature of the relevance of particular statements in the text to the patient encounter or medical topic to which the text relates. A statistical knowledge representation model may then be trained to form associations based on the prevalence of particular labels corresponding to similar text within an aggregate set of multiple marked up documents. For example, if "pneumothorax" is labeled as a "complication" in a large enough proportion of clinical procedure reports documenting pacemaker implantation procedures, a statistical knowledge representation model may generate and store a concept relationship that "pneumothorax is-complication-of pacemaker implantation." In some embodiments, automatically generated and hard coded (e.g., by a human developer) concepts and/or relationships may both be included in a knowledge representation model used by fact extraction component 104.

As discussed above, it should be appreciated that aspects of the invention are not limited to any particular technique(s) for constructing knowledge representation models. Examples of suitable techniques include those disclosed in the following:

Gómez-Pérez, A., and Manzano-Macho, D. (2005). *An overview of methods and tools for ontology learning from texts*. Knowledge Engineering Review 19, p. 187-212.

Cimiano, P., and Staab, S. (2005). *Learning concept hierarchies from text with a guided hierarchical clustering algorithm*. In C. Biemann and G. Paas (eds.), Proceedings of the ICML 2005 Workshop on Learning and Extending Lexical Ontologies with Machine Learning Methods, Bonn, Germany.

Fan, J., Ferrucci, D., Gondek, D., and Kalyanpur, A. (2010). *PRISMATIC: Inducing Knowledge from a Lange Scale Lexicalized Relation Resource*. NAACL Workshop on Formalisms and Methodology for Learning by Reading.

Welty, C., Fan, J., Gondek, D. and Schlaikjer, A. (2010). *Large scale relation detection*. NAACL Workshop on Formalisms and Methodology for Learning by Reading.

Each of the foregoing publications is incorporated herein by reference in its entirety.

Alternatively or additionally, in some embodiments a fact extraction component may make use of one or more statistical models to extract semantic entities from natural language input. In general, a statistical model can be described as a functional component designed and/or trained to analyze new inputs based on probabilistic patterns observed in prior training inputs. In this sense, statistical models differ from "rule-based" models, which typically apply hard-coded deterministic rules to map from inputs having particular characteristics to particular outputs. By contrast, a statistical model may operate to determine a particular output for an input with particular characteristics by considering how often (e.g., with what probability) training inputs with those same characteristics (or similar characteristics) were associated with that particular output in the statistical model's training data. To supply the probabilistic data that allows a statistical model to extrapolate from the tendency of particular input characteristics to be associated with particular outputs in past examples, statistical models are typically trained (or "built") on large training corpuses with great numbers of example inputs. Typically the example inputs are labeled with the known outputs with which they should be associated, usually by a human labeler with expert knowledge of the domain. Characteristics of interest (known as "features") are identified ("extracted") from the inputs, and the statistical model learns the probabilities with which different features are associated with different outputs, based on how often training inputs with those features are associated with those outputs. When the same features are extracted from a new input (e.g., an input that has not been labeled with a known output by a human), the statistical model can then use the learned probabilities for the extracted features (as learned from the training data) to determine which output is most likely correct for the new input. Exemplary implementations of a fact extraction component using one or more statistical models are described further below.

In some embodiments, fact extraction component 104 may utilize a statistical fact extraction model based on entity detection and/or tracking techniques, such as those disclosed in: Florian, R., Hassan, H., Ittycheriah, A., Jing, H., Kambhatla, N., Luo, X., Nicolov, N., and Roukos, S. (2004). *A Statistical Model for Multilingual Entity Detection and Tracking*. Proceedings of the Human Language Technologies Conference 2004 (HLT-NAACL'04). This publication is incorporated herein by reference in its entirety.

For example, in some embodiments, a list of fact types of interest for generating medical reports may be defined, e.g., by a developer of fact extraction component 104. Such fact types (also referred to herein as "entity types") may include, for example, problems, disorders (a disorder is a type of problem), diagnoses (a diagnosis may be a disorder that a clinician has identified as a problem for a particular patient), findings (a finding is a type of problem that need not be a disorder), medications, body sites, social history facts, allergies, diagnostic test results, vital signs, procedures, procedure steps, observations, devices, and/or any other suitable medical fact types. It should be appreciated that any suitable list of fact types may be utilized, and may or may not include any of the fact types listed above, as aspects of the invention are not limited in this respect. In some embodiments, spans of text in a set of sample patient encounter reports may be labeled (e.g., by a human) with appropriate fact types from the list. A statistical model may then be trained on the corpus of labeled sample reports to detect and/or track such fact types as semantic entities, using entity detection and/or tracking techniques, examples of which are described below.

For example, in some embodiments, a large number of past free-form narrations created by clinicians may be manually labeled to form a corpus of training data for a statistical entity detection model. As discussed above, in some embodiments, a list of suitable entities may be defined (e.g., by a domain administrator) to include medical fact types that are to be extracted from future clinician narrations. One or more human labelers (e.g., who may have specific knowledge about medical information and typical clinician narration content) may then manually label portions of the training texts with the particular defined entities to which they correspond. For example, given the training text, "Patient is complaining of acute sinusitis," a human labeler may label the text portion "acute sinusitis" with the entity label "Problem." In another example, given the training text, "He has sinusitis, which appears to be chronic," a human labeler may label the text "sinusitis" and "chronic" with a single label indicating that both words together correspond to a "Problem" entity. As should be clear from these examples, the portion of the text labeled as corresponding to a single conceptual entity need not be formed of contiguous words, but may have words split up within the text, having non-entity words in between.

In some embodiments, the labeled corpus of training data may then be processed to build a statistical model trained to detect mentions of the entities labeled in the training data. Each time the same conceptual entity appears in a text, that appearance is referred to as a mention of that entity. For example, consider the text, "Patient has sinusitis. His sinusitis appears to be chronic." In this example, the entity detection model may be trained to identify each appearance of the word "sinusitis" in the text as a separate mention of the same "Problem" entity.

In some embodiments, the process of training a statistical entity detection model on labeled training data may involve a number of steps to analyze each training text and probabilistically associate its characteristics with the corresponding entity labels. In some embodiments, each training text (e.g., free-form clinician narration) may be tokenized to break it down into various levels of syntactic substructure. For example, in some embodiments, a tokenizer module may be implemented to designate spans of the text as representing structural/syntactic units such as document sections, paragraphs, sentences, clauses, phrases, individual tokens, words, sub-word units such as affixes, etc. In some embodiments, individual tokens may often be single words, but some tokens may include a sequence of more than one word that is defined, e.g., in a dictionary, as a token. For example, the term "myocardial infarction" could be defined as a token, although it is a sequence of more than one word. In some embodiments, a token's identity (i.e., the word or sequence of words itself) may be used as a feature of that token. In some embodiments, the token's placement within particular syntactic units in the text (e.g., its section, paragraph, sentence, etc.) may also be used as features of the token.

In some embodiments, an individual token within the training text may be analyzed (e.g., in the context of the surrounding sentence) to determine its part of speech (e.g., noun, verb, adjective, adverb, preposition, etc.), and the token's part of speech may be used as a further feature of that token. In some embodiments, each token may be tagged with its part of speech, while in other embodiments, not every token may be tagged with a part of speech. In some embodiments, a list of relevant parts of speech may be pre-defined, e.g., by a developer of the statistical model, and any token having a part of speech listed as relevant may be tagged with that part of speech. In some embodiments, a parser module may be implemented to determine the syntactic structure of sentences in the text, and to designate positions within the sentence structure as features of individual tokens. For example, in some embodiments, the fact that a token is part of a noun phrase or a verb phrase may be used as a feature of that token. Any type of parser may be used, non-limiting examples of which include a bottom-up parser and/or a dependency parser, as aspects of the invention are not limited in this respect. In some embodiments, section membership may be used as a feature of a token.

In some embodiments, a section normalization module may be implemented to associate various portions of the narrative text with the proper section to which it should belong. In some embodiments, a set of standardized section types (e.g., identified by their section headings) may be defined for all texts, or a different set of normalized section headings may be defined for each of a number of different types of texts (e.g., corresponding to different types of documents). For example, in some embodiments, a different set of normalized section headings may be defined for each type of medical document in a defined set of medical document types. Non-limiting examples of medical document types include consultation reports, history & physical reports, discharge summaries, and emergency room reports, although there are also many other examples. In the medical field, the various types of medical documents are often referred to as "work types." In some cases, the standard set of sections for various types of medical documents may be established by a suitable system standard, institutional standard, or more widely applicable standard, such as the Meaningful Use standard (discussed above) or the Logical Observation Identifiers Names and Codes (LOINC) standard maintained by the Regenstrief Institute. For example, an expected set of section headings for a history & physical report under the Meaningful Use standard may include headings for a "Reason for Visit" section, a "History of Present Illness" section, a "History of Medication Use" section, an "Allergies, Adverse Reactions and Alerts" section, a "Review of Systems" section, a "Social History" section, a "Physical Findings" section, an "Assessment and Plan" section, and/or any other suitable section(s). Any suitable set of sections may be used, however, as aspects of the invention are not limited in this respect.

A section normalization module may use any suitable technique to associate portions of text with normalized document sections, as aspects of the invention are not limited in this respect. In some embodiments, the section normalization module may use a table (e.g., stored as data in a storage medium) to map text phrases that commonly occur in medical documents to the sections to which they should belong. In another example, a statistical model may be trained to determine the most likely section for a portion of text based on its semantic content, the semantic content of surrounding text portions, and/or the expected semantic content of the set of normalized sections. In some embodiments, once a normalized section for a portion of text has been identified, the membership in that section may be used as a feature of one or more tokens in that portion of text.

In some embodiments, other types of features may be extracted, i.e., identified and associated with tokens in the training text. For example, in some embodiments, an N-gram feature may identify the previous (N−1) words and/or tokens in the text as a feature of the current token. In another example, affixes (e.g., suffixes such as -ectomy, -oma, -itis, etc.) may be used as features of tokens. In another example, one or more predefined dictionaries and/or ontologies may be accessed, and a token's membership in any of those dictionaries may be used as a feature of that token. For example, a predefined dictionary of surgical procedures may be accessed, and/or a dictionary of body sites, and/or a dictionary of known diseases, etc. It should be appreciated, however, that all of the foregoing feature types are merely examples, and any suitable number and/or types of features of interest may be designated, e.g., by a developer of the statistical entity detection model, as aspects of the invention are not limited in this respect.

In some embodiments, the corpus of training text with its hand-labeled fact type entity labels, along with the collection of features extracted for tokens in the text, may be input to the statistical entity detection model for training. As discussed above, examples of suitable features include position within document structure, syntactic structure, parts of speech, parser features, N-gram features, affixes (e.g., prefixes and/or suffixes), membership in dictionaries (sometimes referred to as "gazetteers") and/or ontologies, surrounding token contexts (e.g., a certain number of tokens to the left and/or right of the current token), orthographic features (e.g., capitalization, letters vs. numbers, etc.), entity labels assigned to previous tokens in the text, etc. As one non-limiting example, consider the training sentence, "Patient is complaining of acute sinusitis," for which the word sequence "acute sinusitis" was hand-labeled as being a "Problem" entity. In one exemplary implementation, features extracted for the token "sinusitis" may include the token identity feature that the word is "sinusitis," a syntactic feature specifying that the token occurred at the end of a sentence (e.g., followed by a period), a part-of-speech feature of "noun," a parser feature that the token is part of a noun phrase ("acute sinusitis"), a trigram feature that the two preceding words are "of acute," an affix feature of "-itis," and a dictionary feature that the token is a member of a predefined dictionary of types of inflammation. It should be appreciated, however, that the foregoing list of features is merely exemplary, as any suitable features may be used. Aspects of the invention are not limited to any of the features listed above, and implementations including some, all, or none of the above features, as well as implementations including features not listed above, are possible.

In some embodiments, given the extracted features and manual entity labels for the entire training corpus as input, the statistical entity detection model may be trained to be able to probabilistically label new texts (e.g., texts not included in the training corpus) with automatic entity labels using the same feature extraction technique that was applied to the training corpus. In other words, by processing the input features and manual entity labels of the training corpus, the statistical model may learn probabilistic relationships between the features and the entity labels. When later presented with an input text without manual entity labels, the statistical model may then apply the same feature extraction techniques to extract features from the input text, and may apply the learned probabilistic relationships to automatically determine the most likely entity labels for word sequences in the input text. Any suitable statistical modeling technique may be used to learn such probabilistic relationships, as aspects of the invention are not limited in this respect. Non-limiting examples of suitable known statistical modeling techniques include machine learning techniques such as maximum entropy modeling, support vector machines, and conditional random fields, among others.

In some embodiments, training the statistical entity detection model may involve learning, for each extracted feature, a probability with which tokens having that feature are associated with each entity type. For example, for the suffix feature "-itis," the trained statistical entity detection model may store a probability p1 that a token with that feature should be labeled as being part of a "Problem" entity, a probability p2 that a token with that feature should be labeled as being part of a "Medication" entity, etc. In some embodiments, such probabilities may be learned by determining the frequency with which tokens having the "-itis" feature were hand-labeled with each different entity label in the training corpus. In some embodiments, the probabilities may be normalized such that, for each feature, the probabilities of being associated with each possible entity (fact type) may sum to 1. However, aspects of the invention are not limited to such normalization. In some embodiments, each feature may also have a probability p0 of not being associated with any fact type, such that the non-entity probability p0 plus the probabilities of being associated with each possible fact type sum to 1 for a given feature. In other embodiments, separate classifiers may be trained for each fact type, and the classifiers may be run in parallel. For example, the "-itis" feature may have probability p1 of being part of a "Problem" entity and probability (1-p1) of not being part of a "Problem" entity, probability p2 of being part of a "Medication" entity and probability (1-p2) of not being part of a "Medication" entity, and so on. In some embodiments, training separate classifiers may allow some word sequences to have a non-zero probability of being labeled with more than one fact type simultaneously; for example, "kidney failure" could be labeled as representing both a Body Site and a Problem. In some embodiments, classifiers may be trained to identify sub-portions of an entity label. For example, the feature "-itis" could have a probability $p_B$ of its token being at the beginning of a "Problem" entity label, a probability $p_I$ of its token being inside a "Problem" entity label (but not at the beginning of the label), and a probability $p_O$ of its token being outside a "Problem" entity label (i.e., of its token not being part of a "Problem" entity).

In some embodiments, the statistical entity detection model may be further trained to weight the individual features of a token to determine an overall probability that it should be associated with a particular entity label. For example, if the token "sinusitis" has n extracted features f1 . . . fn having respective probabilities p1 . . . pn of being associated with a "Problem" entity label, the statistical model may be trained to apply respective weights w1 . . . wn to the feature probabilities, and then combine the weighted feature probabilities in any suitable way to determine the overall probability that "sinusitis" should be part of a "Problem" entity. Any suitable technique for determining such weights may be used, including known modeling techniques such as maximum entropy modeling, support vector machines, conditional random fields, and/or others, as aspects of the invention are not limited in this respect.

In some embodiments, when an unlabeled text is input to the trained statistical entity detection model, the model may process the text to extract features and determine probabilities for individual tokens of being associated with various entity (e.g., fact type) labels. In some embodiments, the most probable label (including the non-entity label, if it is most probable) may be selected for each token in the input text. In other embodiments, labels may be selected through more contextual analysis, such as at the phrase level or sentence level, rather than at the token level. Any suitable technique, such as Viterbi techniques, or any other suitable technique, may be used, as aspects of the invention are not limited in this respect. In some embodiments, a lattice may be constructed of the associated probabilities for all entity types for all tokens in a sentence, and the best (e.g., highest combined probability) path through the lattice may be selected to determine which word sequences in the sentence are to be automatically labeled with which entity (e.g., fact type) labels. In some embodiments, not only the best path may be identified, but also the (N−1)-best alternative paths with the next highest associated probabilities. In some embodiments, this may result in an N-best list of alternative hypotheses for fact type labels to be associated with the same input text.

In some embodiments, a statistical model may also be trained to associate fact types extracted from new reports with particular facts to be extracted from those reports (e.g., to determine a particular concept represented by the text portion that has been labeled as an entity mention). For example, in some embodiments, a statistical fact extraction model may be applied to automatically label "acute sinusitis" not only with the "Problem" entity (fact type) label, but also with a label indicating the particular medical fact (e.g., concept) indicated by the word sequence (e.g., the medical fact "sinusitis, acute"). In such embodiments, for example, a single statistical model may be trained to detect specific particular facts as individual entities. For example, in some embodiments, the corpus of training text may be manually labeled by one or more human annotators with labels indicating specific medical facts, rather than labels indicating more general entities such as fact types or categories. However, in other embodiments, the process of detecting fact types as entities may be separated from the process of relating detected fact types to particular facts. For example, in some embodiments, a separate statistical model (e.g., an entity detection model) may be trained to automatically label portions of text with fact type labels, and another separate statistical model (e.g., a relation model) may be trained to identify which labeled entity (fact type) mentions together indicate a single specific medical fact. In some cases, the relation model may identify particular medical facts by relating together two or more mentions labeled with the same entity type.

For example, in the text, "Patient is complaining of acute sinusitis," in some embodiments an entity detection model may label the tokens "acute" and "sinusitis" as being part of a "Problem" entity. In some embodiments, a relation model, given that "acute" and "sinusitis" have been labeled as "Problem," may then relate the two tokens together to a single medical fact of "sinusitis, acute." For another example, consider the text, "Patient has sinusitis, which appears to be chronic." In some embodiments, an entity detection model may be applied to label the tokens "sinusitis" and "chronic" as "Problem" entity mentions. In some embodiments, a relation model may then be applied to determine that the two "Problem" entity mentions "sinusitis" and "chronic" are related (even though they are not contiguous in the text) to represent a single medical fact of "sinusitis, chronic." For yet another example, consider the text, "She has acute sinusitis; chronic attacks of asthma may be a factor." In some embodiments, an entity detection model may label each of the tokens "acute," "sinusitis," "chronic," and "asthma" as belonging to "Problem" entity mentions. In some embodiments, a relation model may then be applied to determine which mentions relate to the same medical fact. For example, the relation model may determine that the tokens "acute" and "sinusitis" relate to a first medical fact (e.g., "sinusitis, acute"), while the tokens "chronic" and "asthma" relate to a different medical fact (e.g., "asthma, chronic"), even though the token "chronic" is closer in the sentence to the token "sinusitis" than to the token "asthma."

In some embodiments, a relation model may be trained statistically using methods similar to those described above for training the statistical entity detection model. For example, in some embodiments, training texts may be manually labeled with various types of relations between entity mentions and/or tokens within entity mentions. For example, in the training text, "Patient has sinusitis, which appears to be chronic," a human annotator may label the "Problem" mention "chronic" as having a relation to the "Problem" mention "sinusitis," since both mentions refer to the same medical fact. In some embodiments, the relation annotations may simply indicate that certain mentions are related to each other, without specifying any particular type of relationship. In other embodiments, relation annotations may also indicate specific types of relations between entity mentions. Any suitable number and/or types of relation annotations may be used, as aspects of the invention are not limited in this respect. For example, in some embodiments, one type of relation annotation may be a "split" relation label. The tokens "sinusitis" and "chronic," for example, may be labeled as having a split relationship, because "sinusitis" and "chronic" together make up an entity, even though they are not contiguous within the text. In this case, "sinusitis" and "chronic" together indicate a specific type of sinusitis fact, i.e., one that it is chronic and not, e.g., acute. Another exemplary type of relation may be an "attribute" relation. In some embodiments, one or more system developers may define sets of attributes for particular fact types, corresponding to related information that may be specified for a fact type. For example, a "Medication" fact type may have attributes "dosage," "route," "frequency," "duration," etc. In another example, an "Allergy" fact type may have attributes "allergen," "reaction," "severity," etc. It should be appreciated, however, that the foregoing are merely examples, and that aspects of the invention are not limited to any particular attributes for any particular fact types. Also, other types of fact relations are possible, including family relative relations, causes-problem relations, improves-problem relations, and many others. Aspects of the invention are not limited to use of any particular relation types.

In some embodiments, using techniques similar to those described above, the labeled training text may be used as input to train the statistical relation model by extracting features from the text, and probabilistically associating the extracted features with the manually supplied labels. Any suitable set of features may be used, as aspects of the invention are not limited in this respect. For example, in some embodiments, features used by a statistical relation model may include entity (e.g., fact type) labels, parts of speech, parser features, N-gram features, token window size (e.g., a count of the number of words or tokens present between two tokens that are being related to each other), and/or any other suitable features. It should be appreciated, however, that the foregoing features are merely exemplary, as embodiments are not limited to any particular list of features. In some embodiments, rather than outputting only the best (e.g., most probable) hypothesis for relations between entity mentions, a statistical relation model may output a list of multiple alternative hypotheses, e.g., with corresponding probabilities, of how the entity mentions labeled in the input text are related to each other. In yet other embodiments, a relation model may be hard-coded and/or otherwise rule-based, while the entity detection model used to label text portions with fact types may be trained statistically.

In some embodiments, the relation model or another statistical model may also be trained to track mentions of the same entity from different sentences and/or document sections and to relate them together. Exemplary techniques for entity tracking are described in the publication by Florian cited above.

In some embodiments, further processing may be applied to normalize particular facts extracted from the text to standard forms and/or codes in which they are to be documented. For example, medical personnel often have many different ways of phrasing the same medical fact, and a normalization/coding process in some embodiments may be applied to identify the standard form and/or code corresponding to each extracted medical fact that was stated in a non-standard way. The standard form and/or code may be derived from any suitable source, as aspects of the invention are not limited in this respect. Some standard terms and/or codes may be derived from a government or profession-wide standard, such as SNOMED (Systematized Nomenclature of Medicine), UMLS (Unified Medical Language System), RxNorm, RadLex, etc. Other standard terms and/or codes may be more locally derived, such as from standard practices of a particular locality or institution. Still other standard terms and/or codes may be specific to the documentation system including the fact extraction component being applied.

For example, given the input text, "His sinuses are constantly inflamed," in some embodiments, an entity detection model together with a relation model (or a single model performing both functions) may identify the tokens "sinuses," "constantly" and "inflamed" as representing a medical fact. In some embodiments, a normalization/coding process may then be applied to identify the standard form for documenting "constantly inflamed sinuses" as "sinusitis, chronic." Alternatively or additionally, in some embodiments the normalization/coding process may identify a standard code used to document the identified fact. For example, the ICD-9 code for "sinusitis, chronic" is ICD-9 code #473. Any suitable coding system may be used, as aspects of the invention are not limited in this respect. Exemplary standard codes include ICD (International Classification of Diseases) codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes.

In some embodiments, a normalization/coding process may be rule-based (e.g., using lists of possible ways of phrasing particular medical facts, and/or using an ontology of medical terms and/or other language units to normalize facts extracted from input text to their standard forms). For example, in some embodiments, the tokens identified in the text as corresponding to a medical fact may be matched to corresponding terms in an ontology. In some embodiments, a list of closest matching terms may be generated, and may be ranked by their similarity to the tokens in the text. The similarity may be scored in any suitable way. For example, in one suitable technique, one or more tokens in the text may be considered as a vector of its component elements, such as words, and each of the terms in the ontology may also be considered as a vector of component elements such as words. Similarity scores between the tokens may then be computed by comparing the corresponding vectors, e.g., by calculating the angle between the vectors, or a related measurement such as the cosine of the angle. In some embodiments, one or more concepts that are linked in the ontology to one or more of the higher ranking terms (e.g., the terms most similar to the identified tokens in the text) may then be identified as hypotheses for the medical fact to be extracted from that portion of the text. Exemplary techniques that may be used in some embodiments are described in Salton, Wong, & Yang: "A vector space model for automatic indexing," Communications of the ACM, November 1975. This publication is incorporated herein by reference in its entirety. However, these are merely examples, and any suitable technique(s) for normalizing entity tokens to standard terms may be utilized in some embodiments, as aspects of the invention are not limited in this respect.

In some embodiments, the normalization/coding process may output a single hypothesis for the standard form and/or code corresponding to each extracted fact. For example, the single output hypothesis may correspond to the concept linked in the ontology to the term that is most similar to the token(s) in the text from which the fact is extracted. However, in other embodiments, the normalization/coding process may output multiple alternative hypotheses, e.g., with corresponding probabilities, for the standard form and/or code corresponding to an individual extracted fact. Thus, it should be appreciated that in some embodiments multiple alternative hypotheses for a medical fact to be extracted from a portion of input text may be identified by fact extraction component 104. Such alternative hypotheses may be collected at any or all of various processing levels of fact extraction, including entity detection, entity relation, and/or normalization/coding stages. In some embodiments, the list of alternative hypotheses may be thresholded at any of the various levels, such that the final list output by fact extraction component 104 may represent the N-best alternative hypotheses for a particular medical fact to be extracted.

It should be appreciated that the foregoing are merely examples, and that fact extraction component 104 may be implemented in any suitable way and/or form, as aspects of the invention are not limited in this respect.

In some embodiments, a user such as clinician 120 may monitor, control and/or otherwise interact with the fact extraction and/or fact review process through a user interface provided in connection with system 100. For example, in some embodiments, user interface 140 may be provided by fact review component 106, e.g., through execution (e.g., by one or more processors of system 100) of programming instructions incorporated in fact review component 106. One exemplary implementation of such a user interface is graphical user interface (GUI) 200, illustrated in FIG. 2. In some embodiments, when the user is clinician 120, GUI 200 may be presented via user interface 110. In some embodiments, a user may be a person other than a clinician; for example, another person such as coding specialist 150 may be presented with GUI 200 via user interface 140. However, it should be appreciated that "user," as used herein, refers to an end user of system 100, as opposed to a software and/or hardware developer of any component of system 100.

The user interface is not limited to a graphical user interface, as other ways of providing data from system 100 to users may be used. For example, in some embodiments, audio indicators may be transmitted from system 100 and conveyed to a user. It should be appreciated that any type of user interface may be provided in connection with fact extraction, fact review and/or other related processes, as aspects of the invention are not limited in this respect. While the exemplary embodiments illustrated in FIG. 1 involve data processing at system 100 and data communication between system 100 and user interfaces 110 and/or 140, it should be appreciated that in other embodiments any or all processing components of system 100 may instead be implemented locally at user interface 110 and/or user interface 140, as aspects of the invention are not limited to any particular distribution of local and/or remote processing capabilities.

As depicted in FIG. 2, GUI 200 includes a number of separate panes displaying different types of data. Identifying information pane 210 includes general information identifying patient 222 as a male patient named John Doe. Such general patient identifying information may be entered by clinician 120, or by other user 150, or may be automatically populated from an electronic medical record for patient 122, or may be obtained from any other suitable source. Identifying information pane 210 also displays the creation date and document type of the report currently being worked on. This information may also be obtained from any suitable source, such as from stored data or by manual entry. When referring herein to entry of data by clinician 120 and/or other user 150, it should be appreciated that any suitable form of data entry may be used, including input via mouse, keyboard, touchscreen, stylus, voice, or any other suitable input form, as aspects of the invention are not limited in this respect.

GUI 200 as depicted in FIG. 2 includes a text panel 220 in which a text narrative referring to the encounter between clinician 120 and patient 122 is displayed. In some embodiments, text panel 220 may include text editor functionality, such that clinician 120 may directly enter the text narrative into text panel 220, either during the patient encounter or at some time thereafter. If ASR is used to produce the text narrative from a spoken dictation provided by clinician 120, in some embodiments the text may be displayed in text panel 220 as it is produced by ASR engine 102, either in real time while clinician 120 is dictating, or with a larger processing delay. In other embodiments, the text narrative may be received as stored data from another source, such as from medical transcriptionist 130, and may be displayed in completed form in text panel 220. In some embodiments, the text narrative may then be edited if desired by clinician 120 and/or other user 150 within text panel 220. However, text editing capability is not required, and in some embodiments text panel 220 may simply display the text narrative without providing the ability to edit it.

Exemplary GUI 200 further includes a fact panel 230 in which one or more medical facts, once extracted from the text narrative and/or entered in another suitable way, may be displayed as discrete structured data items. When clinician 120 and/or other user 150 is ready to direct fact extraction component 104 to extract one or more medical facts from the text narrative, in some embodiments he or she may select process button 240 via any suitable selection input method. However, a user indication to begin fact extraction is not limited to a button such as process button 240, as any suitable way to make such an indication may be provided by GUI 200. In some embodiments, no user indication to begin fact extraction may be required, and fact extraction component 104 may begin a fact extraction process as soon as a requisite amount of text (e.g., enough text for fact extraction component 104 to identify one or more clinical facts that can be ascertained therefrom) is entered and/or received. In some embodiments, a user may select process button 240 to cause fact extraction to be performed before the text narrative is complete. For example, clinician 120 may dictate, enter via manual input and/or otherwise provide a part of the text narrative, select process button 240 to have one or more facts extracted from that part of the text narrative, and then continue to provide further part(s) of the text narrative. In another example, clinician 120 may provide all or part of the text narrative, select process button 240 and review the resulting extracted facts, edit the text narrative within text pane 220, and then select process button 240 again to review how the extracted facts may change.

Figure 3B:
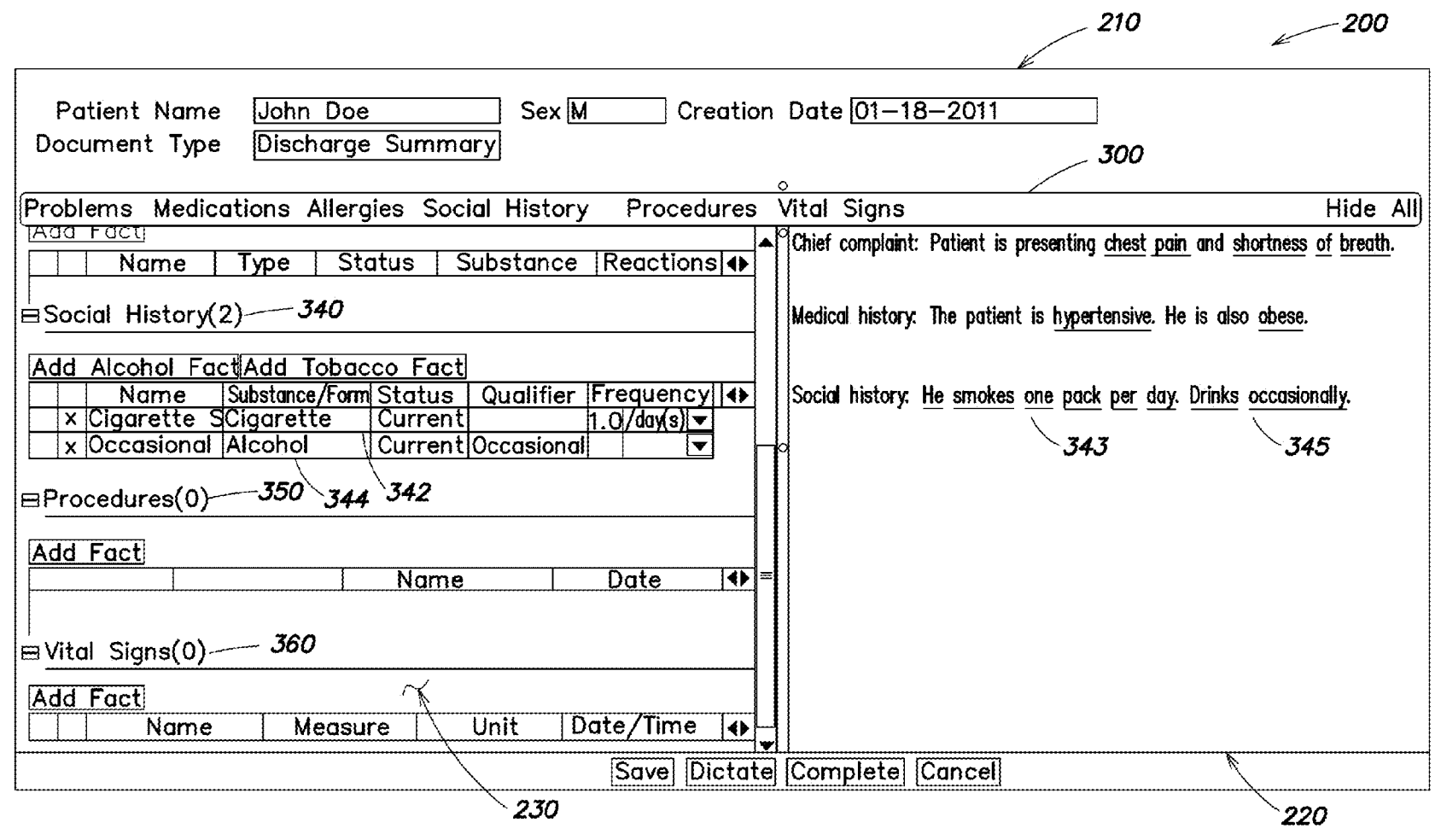

In some embodiments, one or more medical facts extracted from the text narrative by fact extraction component 104 may be displayed to the user via GUI 200 in fact panel 230. Screenshots illustrating an example display of medical facts extracted from an example text narrative are provided in FIGS. 3A and 3B. FIG. 3A is a screenshot with fact panel 230 scrolled to the top of a display listing medical facts extracted from the example text narrative, and FIG. 3B is a screenshot with fact panel 230 scrolled to the bottom of the display listing the extracted medical facts. In some embodiments, as depicted in FIGS. 3A and 3B, medical facts corresponding to a patient encounter may be displayed in fact panel 230, and organized into a number of separate categories of types of facts. An exemplary set of medical fact categories includes categories for problems, medications, allergies, social history, procedures and vital signs. However, it should be appreciated that any suitable fact categories may be used, as aspects of the invention are not limited in this respect. In addition, organization of facts into categories is not required, and displays without such organization are possible. As depicted in FIGS. 3A and 3B, in some embodiments GUI 200 may be configured to provide a navigation panel 300, with a selectable indication of each fact category available in the display of fact panel 230. In some embodiments, when the user selects one of the categories within navigation panel 300 (e.g., by clicking on it with a mouse, touchpad, stylus, or other input device), fact panel 230 may be scrolled to display the corresponding fact category. As depicted in FIGS. 3A and 3B, all available fact categories for the current document type are displayed, even if a particular fact category includes no extracted or otherwise entered medical facts. However, this is not required; in some embodiments, only those fact categories having facts ascertained from the patient encounter may be displayed in fact panel 230.

Fact panel 230 scrolled to the top of the display as depicted in FIG. 3A shows problem fact category 310, medications fact category 320, and allergies fact category 330. Within problem fact category 310, four clinical facts have been extracted from the example text narrative; no clinical facts have been extracted in medications fact category 320 or in allergies fact category 330. Within problem fact category 310, fact 312 indicates that patient 122 is currently presenting with unspecified chest pain; that the chest pain is a currently presenting condition is indicated by the status "active". Fact 314 indicates that patient 122 is currently presenting with shortness of breath. Fact 316 indicates that the patient has a history (status "history") of unspecified essential hypertension. Fact 318 indicates that the patient has a history of unspecified obesity. As illustrated in FIG. 3A, each clinical fact in problem fact category 310 has a name field and a status field. In some embodiments, each field of a clinical fact may be a structured component of that fact represented as a discrete structured data item. In this example, the name field may be structured such that only a standard set of medical terms for problems may be available to populate that field. For example, the status field may be structured such that only statuses in the Systematized Nomenclature of Medicine (SNOMED) standard (e.g., "active" and "history") may be selected within that field, although other standards (or no standard) could be employed. An exemplary list of fact categories and their component fields is given below. However, it should be appreciated that this list is provided by way of example only, as aspects of the invention are not limited to any particular organizational system for facts, fact categories and/or fact components.

Exemplary list of fact categories and component fields:
Category: Problems. Fields: Name, SNOMED status, ICD code.
Category: Medications. Fields: Name, Status, Dose form, Frequency, Measures, RxNorm code, Administration condition, Application duration, Dose route.
Category: Allergies. Fields: Allergen name, Type, Status, SNOMED code, Allergic reaction, Allergen RxNorm.
Category: Social history—Tobacco use. Fields: Name, Substance, Form, Status, Qualifier, Frequency, Duration, Quantity, Unit type, Duration measure, Occurrence, SNOMED code, Norm value, Value.
Category: Social history—Alcohol use. Fields: Name, Substance, Form, Status, Qualifier, Frequency, Duration, Quantity, Quantifier, Unit type, Duration measure, Occurrence, SNOMED code, Norm value, Value.
Category: Procedures. Fields: Name, Date, SNOMED code.
Category: Vital signs. Fields: Name, Measure, Unit, Unit type, Date/Time, SNOMED code, Norm value, Value.

In some embodiments, a linkage may be maintained between one or more medical facts extracted by fact extraction component 104 and the portion(s) of the text narrative from which they were extracted. As discussed above, such a portion of the text narrative may consist of a single word or may include multiple words, which may be in a contiguous sequence or may be separated from each other by one or more intervening words, sentence boundaries, section boundaries, or the like. For example, fact 312 indicating that patient 122 is currently presenting with unspecified chest pain may have been extracted by fact extraction component 104 from the words "chest pain" in the text narrative. The "active" status of extracted fact 312 may have been determined by fact extraction component 104 based on the appearance of the words "chest pain" in the section of the text narrative with the section heading "Chief complaint". In some embodiments, fact extraction component 104 and/or another processing component may be programmed to maintain (e.g., by storing appropriate data) a linkage between an extracted fact (e.g., fact 312) and the corresponding text portion (e.g., "chest pain").

In some embodiments, GUI 200 may be configured to provide visual indicators of the linkage between one or more facts displayed in fact panel 230 and the corresponding portion(s) of the text narrative in text panel 220 from which they were extracted. In the example depicted in FIG. 3A, the visual indicators are graphical indicators consisting of lines placed under the appropriate portions of the text narrative in text panel 220. Indicator 313 indicates the linkage between fact 312 and the words "chest pain" in the "Chief complaint" section of the text narrative; indicator 315 indicates the linkage between fact 314 and the words "shortness of breath" in the "Chief complaint" section of the text narrative; indicator 317 indicates the linkage between fact 316 and the word "hypertensive" in the "Medical history" section of the text narrative; and indicator 319 indicates the linkage between fact 318 and the word "obese" in the "Medical history" section of the text narrative. However, these are merely examples of one way in which visual indicators may be provided, as other types of visual indicators may be provided. For example, different or additional types of graphical indicators may be provided, and/or linked text in text panel 220 may be displayed in a distinctive textual style (e.g., font, size, color, formatting, etc.). Aspects of the invention are not limited to any particular type of linkage indicator.

In some embodiments, when the textual representation of the free-form narration provided by clinician 120 has been re-formatted and fact extraction has been performed with reference to the re-formatted version, the original version may nevertheless be displayed in text panel 220, and linkages may be maintained and/or displayed with respect to the original version. For example, in some embodiments, each extracted clinical fact may be extracted by fact extraction component 104 from a corresponding portion of the re-formatted text, but that portion of the re-formatted text may have a corresponding portion of the original text of which it is a formatted version. A linkage may therefore be maintained between that portion of the original text and the extracted fact, despite the fact actually having been extracted from the re-formatted text. In some embodiments, providing an indicator of the linkage between the extracted fact and the original text may allow clinician 120 and/or other user 150 to appreciate how the extracted fact is related to what was actually said in the free-form narration. However, other embodiments may maintain linkages between extracted facts and the re-formatted text, as an alternative or in addition to the linkages between the extracted facts and the original text, as aspects of the invention are not limited in this respect.

Fact panel 230 scrolled to the bottom of the display as depicted in FIG. 3B shows social history fact category 340, procedures fact category 350, and vital signs fact category 360. Within social history fact category 340, two clinical facts have been extracted; no facts have been extracted in procedures fact category 350 and vital signs fact category 360. Within social history fact category 340, fact 342 indicates that patient 122 currently smokes cigarettes with a frequency of one pack per day. Fact 344 indicates that patient 122 currently occasionally drinks alcohol. Indicator 343 indicates that fact 342 was extracted from the words "He smokes one pack per day" in the "Social history" section of the text narrative; and indicator 345 indicates that fact 344 was extracted from the words "Drinks occasionally" in the "Social history" section of the text narrative. In some embodiments, visual indicators such as indicators 343 and 345 may be of a different textual and/or graphical style or of a different indicator type than visual indicators such as indicators 313, 315, 317 and 319, to indicate that they correspond to a different fact category. For example, in some embodiments indicators 343 and 345 corresponding to social history fact category 340 may be displayed in a different color than indicators 313, 315, 317 and 319 corresponding to problems fact category 310. In some embodiments, linkages for different individual facts may be displayed in different textual and/or graphical styles or indicator types to allow the user to easily appreciate which fact corresponds to which portion of the text narrative. For example, in some embodiments indicator 343 may be displayed in a different color than indicator 345 because they correspond to different facts, even though both correspond to the same fact category.

Figure 4:
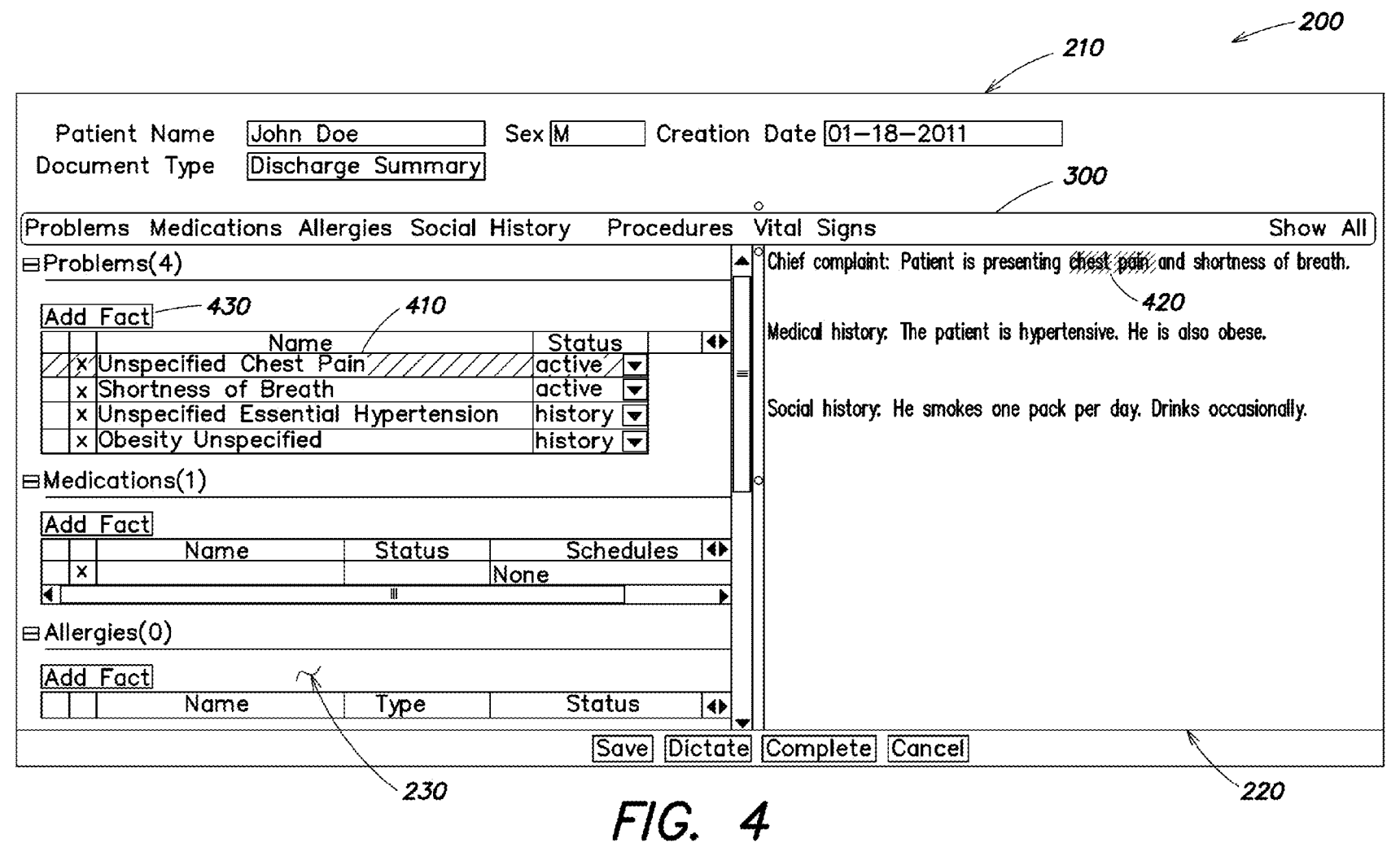

In some embodiments, GUI 200 may be configured to allow the user to select one or more of the medical facts in fact panel 230, and in response to the selection, to provide an indication of the portion(s) of the text narrative from which those fact(s) were extracted. An example is illustrated in FIG. 4. In this example, fact 312 ("unspecified chest pain") has been selected by the user in fact panel 230, and in response visual indicator 420 of the portion of the text narrative from which fact 312 was extracted ("chest pain") is provided. Such a user selection may be made in any suitable way, as aspects of the invention are not limited in this respect. Examples include using an input device (e.g., mouse, keyboard, touchpad, stylus, etc.) to click on or otherwise select fact 312, hovering the mouse or other input mechanism above or nearby to fact 312, speaking a selection of fact 312 through voice, and/or any other suitable selection method. Similarly, in some embodiments GUI 200 may be configured to visually indicate the corresponding fact in fact panel 230 when the user selects a portion of the text narrative in text panel 220. In some embodiments, a visual indicator may include a line or other graphical connector between a fact and its corresponding portion of the text narrative. Any visual indicator may be provided in any suitable form (examples of which are given above) as aspects of the invention are not limited in this respect. In addition, aspects of the invention are not limited to visual indicators, as other forms of indicators may be provided. For example, in response to a user selection of fact 312, an audio indicator of the text portion "chest pain" may be provided in some embodiments. In some embodiments, the audio indicator may be provided by playing the portion of the audio recording of the clinician's spoken dictation comprising the words "chest pain". In other embodiments, the audio indicator may be provided by playing an audio version of the words "chest pain" generated using automatic speech synthesis. Any suitable form of indicator or technique for providing indicators may be used, as aspects of the invention are not limited in this respect.

In some embodiments, GUI 200 may be configured to provide any of various ways for the user to make one or more changes to the set of medical facts extracted from the text narrative by fact extraction component 104 and displayed in fact panel 230, and these changes may be collected by fact review component 106 and applied to the documentation of the patient encounter. For example, the user may be allowed to delete a fact from the set in fact panel 230, e.g., by selecting the "X" option appearing next to the fact. In some embodiments, the user may be allowed to edit a fact within fact panel 230. In one example, the user may edit the name field of fact 312 by selecting the fact and typing, speaking or otherwise providing a different name for that fact. As depicted in FIG. 3A and FIG. 4, in some embodiments the user may edit the status field of fact 312 by selecting a different status from the available drop-down menu, although other techniques for allowing editing of the status field are possible. In some embodiments, the user may alternatively or additionally be allowed to edit a fact by interacting with the text narrative in text panel 220. For example, the user may add, delete, or change one or more words in the text narrative, and then the text narrative may be re-processed by fact extraction component 104 to extract an updated set of medical facts. In some embodiments, the user may be allowed to select only a part of the text narrative in text panel 220 (e.g., by highlighting it), and have fact extraction component 104 re-extract facts only from that part, without disturbing facts already extracted from other parts of the text narrative.

Figure 5:
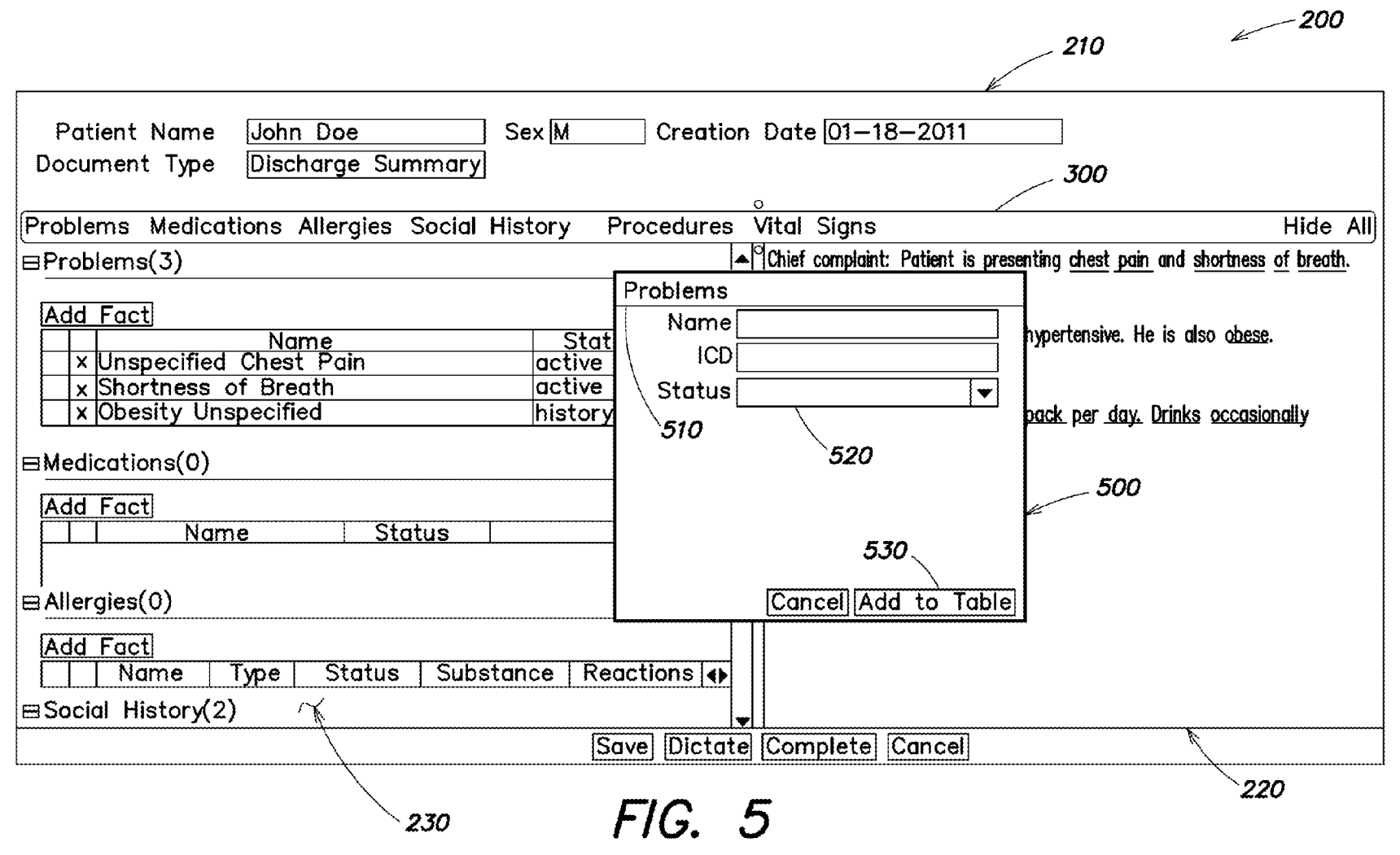

In some embodiments, GUI 200 may be configured to provide any of various ways for one or more facts to be added as discrete structured data items. As depicted in FIG. 4, GUI 200 in some embodiments may be configured to provide an add fact button for each fact category appearing in fact panel 230; one such add fact button is add fact button 430. When the user selects add fact button 430, in some embodiments GUI 200 may provide the user with a way to enter information sufficient to populate one or more fields of a new fact in that fact category, for example by displaying pop-up window 500 as depicted in FIG. 5. It should be appreciated that this is merely one example, as aspects of the invention are not limited to the use of pop-up windows or any other particular method for adding a fact. In this example, pop-up window 500 includes a title bar 510 that indicates the fact category ("Problems") to which the new fact will be added. Pop-up window 500 also provides a number of fields 520 in which the user may enter information to define the new fact to be added. Fields 520 may be implemented in any suitable form, including as text entry boxes, drop-down menus, radio buttons and/or checkboxes, as aspects of the invention are not limited to any particular way of receiving input defining a fact. Finally, pop-up window 500 includes add button 530, which the user may select to add the newly defined fact to the set of facts corresponding to the patient encounter, thus entering the fact as a discrete structured data item.

In some embodiments, GUI 200 may alternatively or additionally be configured to allow the user to add a new fact by selecting a (not necessarily contiguous) portion of the text narrative in text panel 220, and indicating that a new fact should be added based on that portion of the text narrative. This may be done in any suitable way. In one example, the user may highlight the desired portion of the text narrative in text panel 220, and right-click on it with a mouse (or perform another suitable input operation), which may cause the designated text to be processed and any relevant facts to be extracted. In other embodiments, the right-click or other input operation may cause a menu to appear. In some embodiments the menu may include options to add the new fact under any of the available fact categories, and the user may select one of the options to indicate which fact category will correspond to the new fact. In some embodiments, an input screen such as pop-up window 500 may then be provided, and the name field may be populated with the words selected by the user from the text narrative. The user may then have the option to further define the fact through one or more of the other available fields, and to add the fact to the set of medical facts for the patient encounter as described above.

In some embodiments, the set of medical facts corresponding to the current patient encounter (each of which may have been extracted from the text narrative or provided by the user as a discrete structured data item) may be added to an existing electronic medical record (such as an EHR) for patient 122, or may be used in generating a new electronic medical record for patient 122. In some embodiments, clinician 120 and/or coding specialist (or other user) 150 may finally approve the set of medical facts before they are included in any patient record; however, aspects of the present invention are not limited in this respect. In some embodiments, when there is a linkage between a fact in the set and a portion of the text narrative, the linkage may be maintained when the fact is included in the electronic medical record. In some embodiments, this linkage may be made viewable by simultaneously displaying the fact within the electronic medical record and the text narrative (or at least the portion of the text narrative from which the fact was extracted), and providing an indication of the linkage in any of the ways described above. Similarly, extracted facts may be included in other types of patient records, and linkages between the facts in the patient records and the portions of text narratives from which they were extracted may be maintained and indicated in any suitable way.

Figure 6:
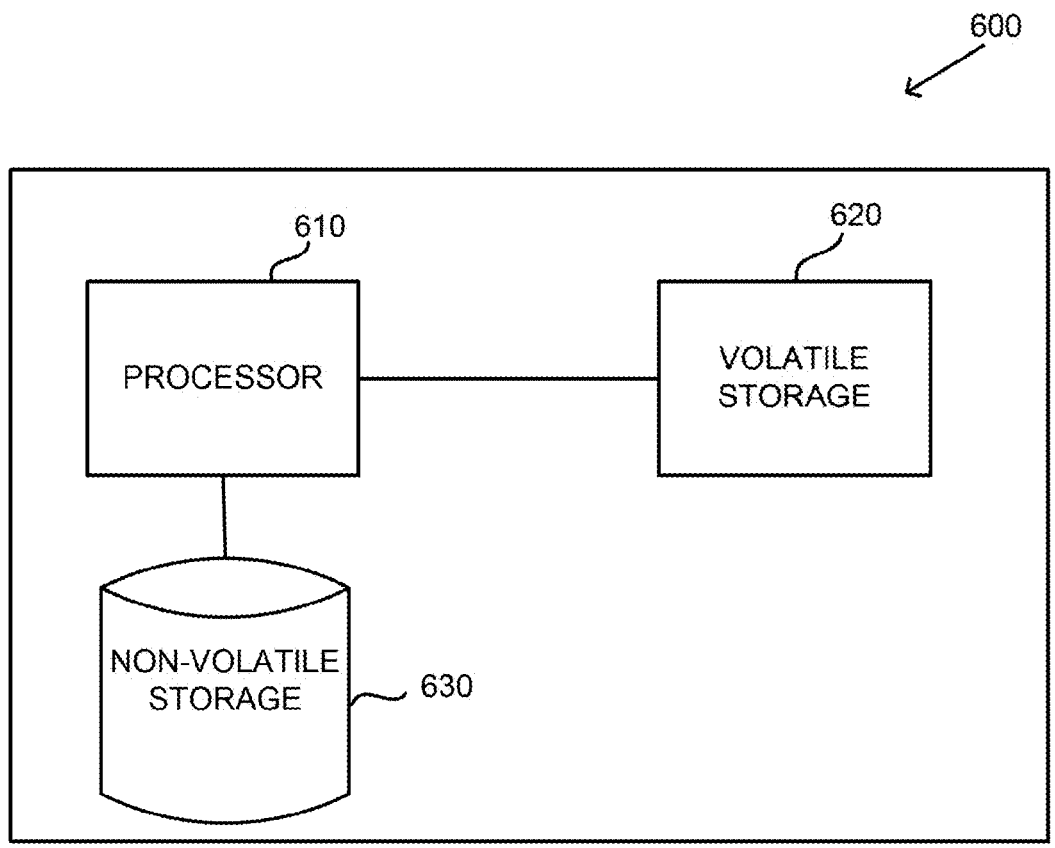
FIG. 6 is a block diagram of an exemplary computer system on which aspects of some embodiments may be implemented.

A CLU system in accordance with the techniques described herein may take any suitable form, as aspects of the present invention are not limited in this respect. An illustrative implementation of a computer system 600 that may be used in connection with some embodiments of the present invention is shown in FIG. 6. One or more computer systems such as computer system 600 may be used to implement any of the functionality described above. The computer system 600 may include one or more processors 610 and one or more tangible, non-transitory computer-readable storage media (e.g., volatile storage 620 and one or more non-volatile storage media 630, which may be formed of any suitable non-volatile data storage media). The processor 610 may control writing data to and reading data from the volatile storage 620 and the non-volatile storage device 630 in any suitable manner, as the aspects of the present invention are not limited in this respect. To perform any of the functionality described herein, the processor 610 may execute one or more instructions stored in one or more computer-readable storage media (e.g., volatile storage 620), which may serve as tangible, non-transitory computer-readable storage media storing instructions for execution by the processor 610.

Computer-Assisted Coding (CAC) System

As discussed above, medical coding has conventionally been a manual process whereby a human professional (the "coder") reads all of the documentation for a patient encounter and enters the appropriate standardized codes (e.g., ICD codes, HCPCS codes, etc.) corresponding to the patient's diagnoses, procedures, etc. The coder is often required to understand and interpret the language of the clinical documents in order to identify the relevant diagnoses, etc., and assign them their corresponding codes, as the language used in clinical documentation often varies widely from the standardized descriptions of the applicable codes. For example, the coder might review a hospital report saying, "The patient coded at 5:23 pm." The coder must then apply the knowledge that "The patient coded" is hospital slang for a diagnosis of "cardiac arrest," which corresponds to ICD-9-CM code 427.5. This diagnosis could not have been identified from a simple word search for the term "cardiac arrest," since that standard term was not actually used in the documentation; more complex interpretation is required in this example.

As also discussed above, conventional medical coding systems may provide a platform on which the human coder can read the relevant documents for a patient encounter, and an interface via which the human coder can manually input the appropriate codes to assign to the patient encounter. By contrast, some embodiments described herein may make use of a type of medical coding system referred to herein as a "computer-assisted coding" (CAC) system, which may automatically analyze medical documentation for a patient encounter to interpret the document text and derive standardized codes hypothesized to be applicable to the patient encounter. The automatically derived codes may then be suggested to the human coder, clinician, or other user of the CAC system. In some embodiments, the CAC system may make use of an NLU engine to analyze the documentation and derive suggested codes, such as through use of one or more components of a CLU system such as exemplary system 100 described above. In some embodiments, the NLU engine may be configured to derive standardized codes as a type of medical fact extracted from one or more documents for the patient encounter, and/or the CLU system may be configured to access coding rules corresponding to the standardized code set(s) and apply the coding rules to extracted medical facts to derive the corresponding codes.

In some embodiments, the CAC system may be configured to provide a user interface via which the automatically suggested codes may be reviewed by a user such as a medical coder. The user interface may take on any of numerous forms, and aspects of the invention are not limited to any particular implementation Like the user interfaces for the CLU system 100 described above, the user interface for the CAC system may provide tools that allow a coder to interact with the CAC system in any suitable form, including visual forms, audio forms, combined forms, or any other form providing the functionality described herein. When the tools are provided in visual form, their functionality may be accessed in some embodiments through a graphical user interface (GUI), which may be implemented in any suitable way. An example of a suitable GUI 700 for a CAC system is illustrated in FIG. 7A.

The exemplary GUI 700 provides the user with the ability to simultaneously view the list of codes for a patient encounter along with the documentation from which the codes are derived. Some embodiments may also allow the user to view structured encounter- or patient-level data such as the patient's age, gender, etc. (not shown in FIG. 7A), some or all of which information may be useful in arriving at the appropriate codes for the patient encounter. In panel 710 is displayed a list of available documents for the patient encounter currently being coded. In the example illustrated in FIG. 7A, these include two History & Physical reports, a Discharge Summary, an Emergency Room Record, a Consultation report, a Progress Note, and an Operative Report. Indicator 712 shows that the current document being viewed is the Discharge Summary dated Jun. 18, 2014, and this document appears in panel 720 where the user can view the text of the document. Shown in panel 730 is the current list of codes for the patient encounter. An indicator 732 shows, for each code in the list, whether the code was automatically suggested or added manually by the user. In this particular example, the empty circles indicate that all of the codes in the current list were automatically suggested by the CAC system.

Exemplary GUI 700 also provides the user with the ability to view and/or query which portion(s) of the available documentation gave rise to the suggestion of which code(s) in the list of codes for the patient encounter. In some embodiments, any suitable indicator(s) may be provided of the link between a particular code and the portion(s) of the documentation text from which the code was derived. Each automatically suggested code may be linked to one or more portions of text from which the code was derived, and each linked portion of text may be linked to one or more codes that are derivable from that portion of text. For instance, viewing together FIGS. 7A and 7D, which show the Discharge Summary viewed at different scroll locations in panel 720, it can be seen that there are two different mentions of "respiratory failure" in the document from which code 518.81 may have been derived (an example of a link between a code and multiple portions of text), and that there are two different codes 303.90 and 571.5 that may have been derived at least in part from the mention of "Alcoholism" in the text (an example of a link between a portion of text and multiple codes).

Figure 7A:
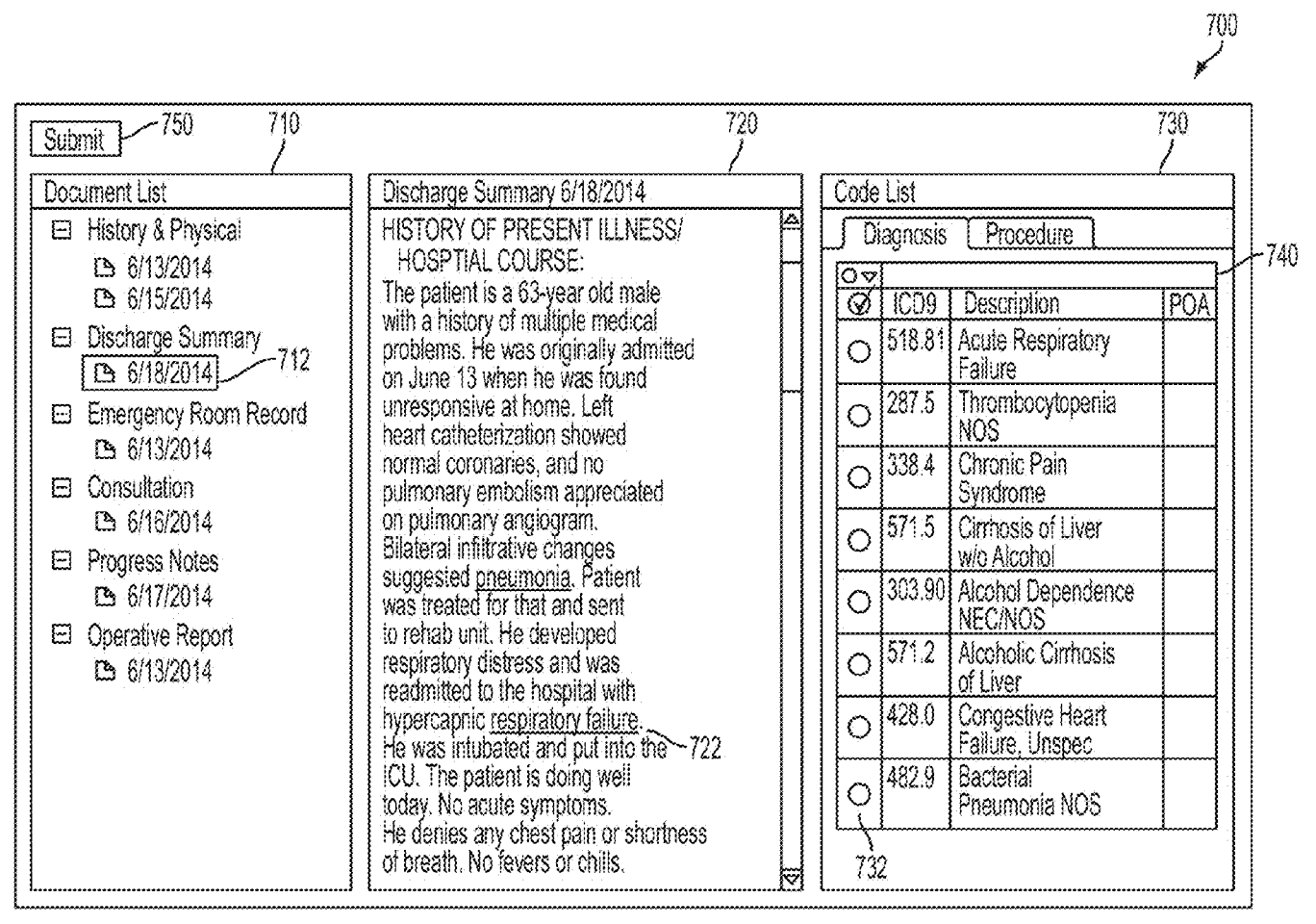

In the example of FIG. 7A, an indicator 722 is provided (underlining in this particular example) to visually distinguish portions of the document text linked to codes in the current list. Exemplary GUI 700 also allows the user to query a particular linked portion of text to see which code(s) are linked to that portion of text. FIG. 7B illustrates an exemplary indicator 724 of the corresponding link that may be displayed in response to the user querying the linked portion of text in any suitable way, such as by selecting or hovering over it with the mouse pointer. Exemplary GUI 700 further allows the user to query a particular code to see which portion(s) of text are linked to that code. FIG. 7C illustrates an exemplary way of querying code 287.5 by right-clicking on the listed code in panel 730 and selecting "Show Highlights" in the context menu that then appears. In response, the document in which the linked text appears is displayed in panel 720 (in this case it is the same Discharge Summary, scrolled to a particular section), and the linked text is visually distinguished by indicator 726 (highlighting in this particular example), as illustrated in FIG. 7D.

If the user disagrees with the linked text and does not believe that the suggested portion(s) of text actually should correspond with the linked code, the user can select "Unlink Text" in the context menu of FIG. 7C to cause the link between that code and the corresponding text to be discarded. The user can also manually create a new link between a code and one or more portions of text, e.g., by selecting "Link Text" in the context menu of FIG. 7C and highlighting or otherwise designating the portion(s) of text in the documentation which should be linked to the selected code.

Exemplary GUI 700 further allows the user to accept or reject each of the automatically suggested codes, e.g., using the context menu of FIG. 7C for each suggested code. FIG. 7E illustrates exemplary indicators 734 and 736 which replace indicator 732 for each code that has been accepted or rejected, respectively. In this example, the user has accepted most of the suggested codes, but has rejected code 571.5 because the user believes the mention of "Alcoholism" in the documentation makes the diagnosis of "Cirrhosis of Liver w/o Alcohol" incorrect. Exemplary GUI 700 further allows the user to provide a reason for the rejection of a code, such as by using the exemplary context menu illustrated in FIG. 7F. In some embodiments, the reasons provided by users for rejecting particular automatically suggested codes may be used for review and/or training purposes (e.g., for training the NLU engine, e.g., of the CLU system to derive more accurate codes from documentation text).

GUI 700 may also allow the user to replace a code with a different code, instead of rejecting the code outright, e.g., using the context menu of FIG. 7C. In the example illustrated in FIG. 7E, the user has replaced code 482.9 with code 482.1, and indicator 738 shows that the new code was user-added. 482.9 (Pneumonia due to *Pseudomonas*) is a more specific diagnosis applicable to the patient encounter than the suggested 482.1 (Bacterial Pneumonia, Unspecified), so the user may provide "More specific code needed" as the reason for the replacement. In some embodiments, when a user replaces an automatically suggested code with a different code, any documentation text that was linked to the originally suggested code may then be linked to the replacement code. Such replacement codes, optionally with linked text and/or replacement reasons, may also be used as feedback, e.g., for training of the CLU system.

The user can also add a code to the list for a patient encounter by manually inputting the code in input field 740. For example, FIG. 7E shows a new code 041.7 that has been added by the user. The user may link the added code to supporting portion(s) of the text, such as the mention of "*pseudomonas*" in the Discharge Summary, e.g., by using the "Link Text" procedure described above.

Figure 8:
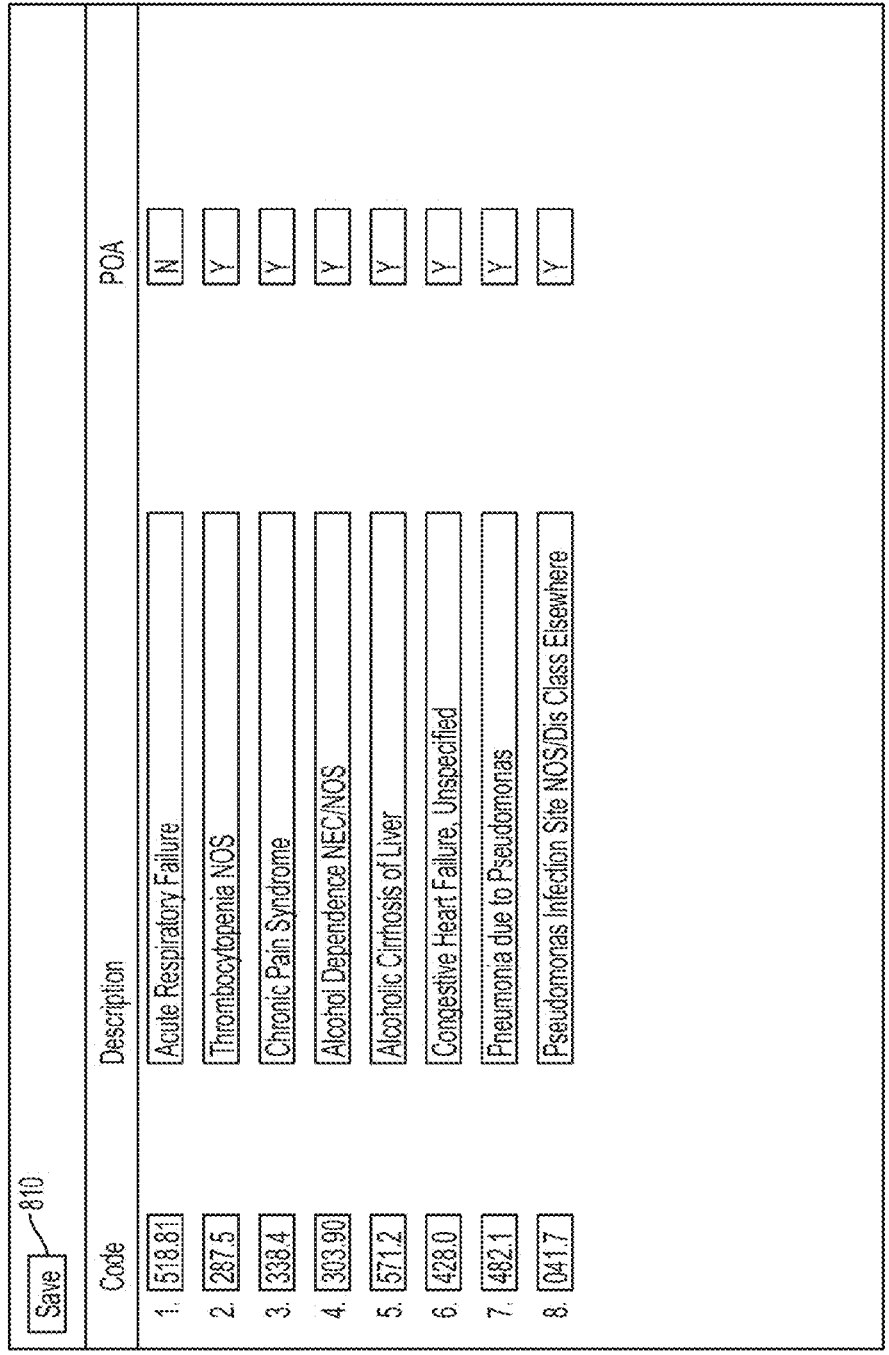
FIG. 8 is a screenshot illustrating an exemplary code finalization screen in accordance with some embodiments.

When the user has completed the review of the codes and supporting documentation, exemplary GUI 700 allows the user to submit the codes for finalization by selecting button 750. FIG. 8 illustrates an exemplary code finalization screen 800 that may be displayed following the user's selection of submit button 750. In exemplary screen 800, all of the accepted and user-added codes are displayed for final review. Alternatively, in some embodiments the user may be required to affirmatively accept even user-added codes before they will appear in code finalization screen 800. The codes are displayed in screen 800 in an ordered sequence, which the user may change by re-ordering the codes. In some embodiments, the order of the finalized sequence of codes may be used in later processes such as billing, to determine the principal diagnosis, etc. Exemplary screen 800 also includes fields for "present on admission" (POA) indicators, which provide information on whether each diagnosis was present when the patient was admitted to the hospital, or was acquired during the hospital stay. This information may be required documentation in some circumstances, and in some embodiments may be used for review and/or training purposes. In some embodiments, POA indicators may be automatically suggested, e.g., using the CLU system; while in other embodiments, POA indicators may only be input manually.

When the user is satisfied with the finalized sequence of codes, exemplary screen 800 provides a button 810 for the codes to be saved, at which the coding process for the patient encounter becomes complete. In some embodiments, the CAC system may compare the finalized sequence of codes with stored coding rules, and may present the user with any applicable error or warning notifications prior to saving. As discussed above, once saved, the finalized sequence of codes may be sent to other processes such as billing and quality review, and in some embodiments may be used for performance review and/or training of the CLU and/or CAC systems.

Figure 9:
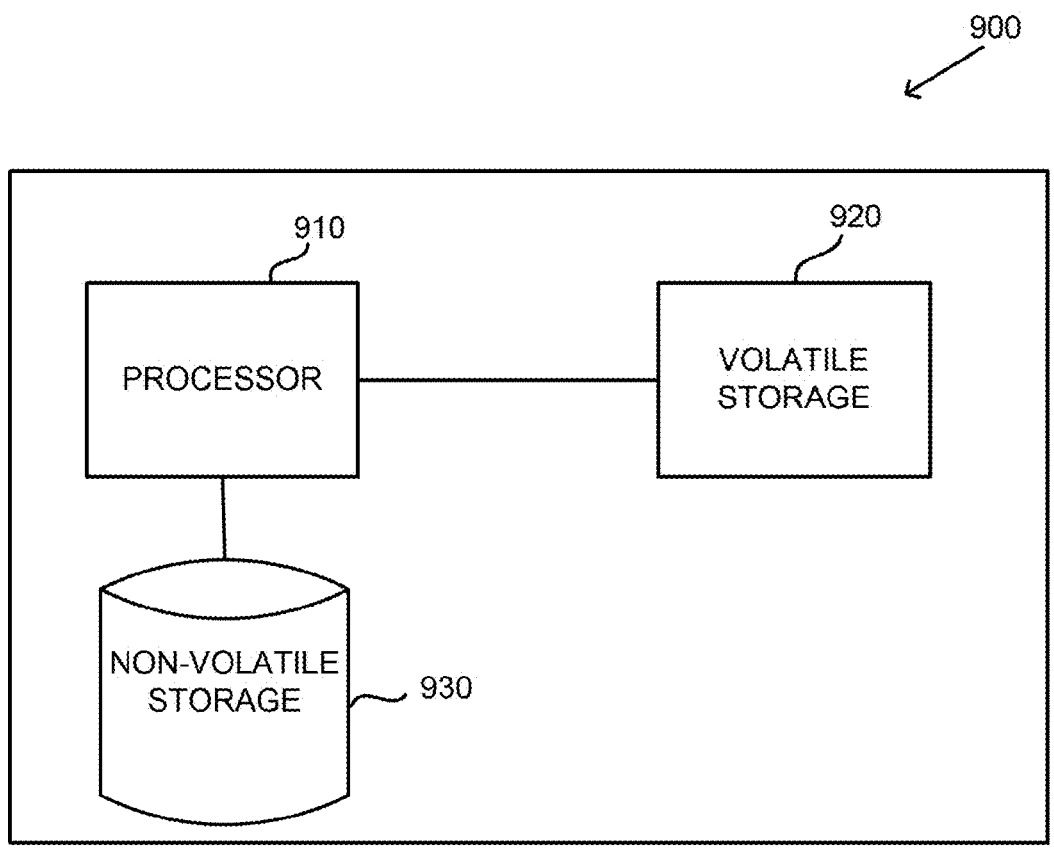
FIG. 9 is a block diagram of an exemplary computer system on which aspects of some embodiments may be implemented.

Like the embodiments of the CLU system 100 described above, the CAC system in accordance with the techniques described herein may take any suitable form, as embodiments are not limited in this respect. An illustrative implementation of a computer system 900 that may be used in connection with some implementations of a CAC system is shown in FIG. 9. One or more computer systems such as computer system 900 may be used to implement any of the functionality of the CAC system described above. As shown, the computer system 900 may include one or more processors 910 and one or more tangible, non-transitory computer-readable storage media (e.g., volatile storage 920 and one or more non-volatile storage media 930, which may be formed of any suitable non-volatile data storage media). The processor 910 may control writing data to and reading data from the volatile storage 920 and the non-volatile storage media 930 in any suitable manner, as the aspects of the present invention are not limited in this respect. To perform any of the functionality described herein, the processor 910 may execute one or more instructions stored in one or more computer-readable storage media (e.g., volatile storage 920), which may serve as tangible, non-transitory computer-readable storage media storing instructions for execution by the processor 910.

Annotation of Richly Formatted Documents

Figure 10:
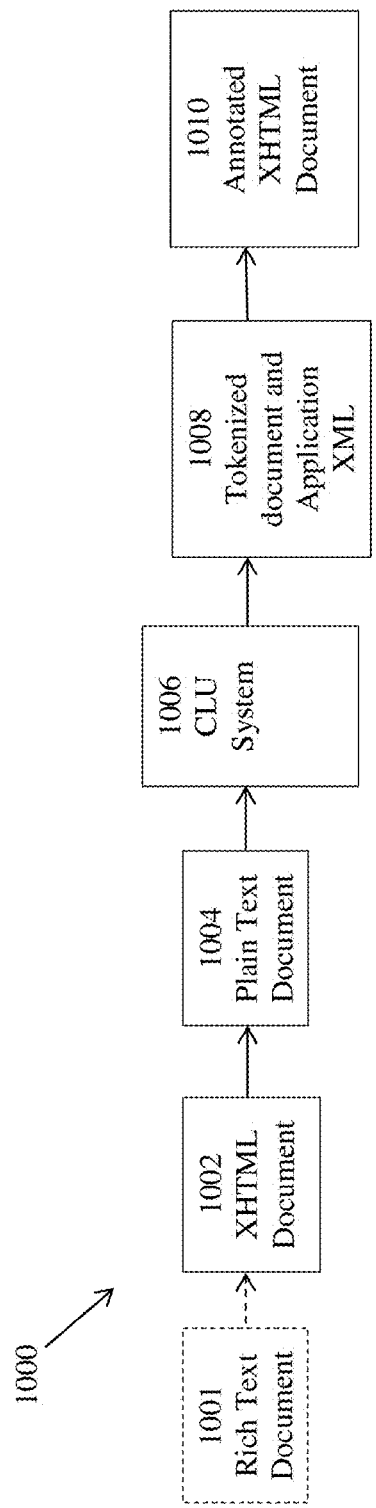
FIG. 10 illustrates a document flow for generating an annotated document, according to a non-limiting embodiment of the present application.

According to an aspect of the present application a system and method are provided for annotating medical documents having a rich format and presenting annotated documents to a user with rich formatting. Referring to FIG. 10, a document flow 1000 may include an XHTML document 1002 representing a medical document and also representing the structure and formatting of a richly formatted document, described further below in connection with rich text document 1001. The medical document may be associated with a clinical patient encounter, and may represent a clinician's notes, a report such as a laboratory or radiology report, or may be any other suitable type of document. As described above, the XHTML document 1002 may represent (or include) rich formatting, such as headings, bold characters, characters in italics, underlining, highlighting, bullet lists, or other formatting.

In at least some instances, an initial medical document may not be in XHTML format. Rather, an initial richly formatted document, such as rich text document 1001 (e.g., representing doctor's notes), may have rich formatting (e.g., of the types described above in connection with document 1002) but may not be a XHTML document. In such instances, the rich text document 1001 (or other richly formatted document) may be converted to the XHTML document 1002 using any suitable conversion device and process.

It may be desirable to annotate the medical document represented by the XHTML document 1002, for instance by generating medical codes corresponding to information expressed in the document. For example, if the medical document represents a summary of a patient encounter, it may be desirable to identify codes implicated by the document relating to diagnoses, medical procedures (including treatments), or other medically relevant information. Such codes may, in some instances, be used for billing purposes and therefore may be medical billing codes. However, other types of annotations, not limited to codes, (such as other types of medical facts that can be extracted by a CLU system as discussed above) may be used as well. As discussed above, the term "annotation" as used herein refers to an item derived from and linked to a portion of text, such as a fact (e.g., a medical fact, one particular example of which may be a medical code such as a medical billing code), a semantic label, or other such item having a link to one or more corresponding portions of text from which it was or could be derived.

It may also be desirable in some embodiments to annotate the medical document automatically (rather than manually). An NLU engine (e.g., forming part of a CLU system) may be used for such purposes. However, NLU engines conventionally are unable to handle rich formatting, being limited to operating on plain text documents. Thus, to annotate the XHTML document 1002, a plain text document 1004 may be generated, for example by extracting the textual information from the XHTML document 1002. Such extraction may include extracting the text nodes from the XHTML document 1002, which may be strung together to form a narrative plain text document represented by plain text document 1004. The plain text document 1004 may retain the content of the XHTML document 1002 but not the formatting.

In generating the plain text document 1004, links may be generated between the span nodes of the XHTML document 1002 and the corresponding position in the plain text document 1004. These links may be maintained to allow later mapping back of annotations from the plain text document 1004 into the XHTML document 1002, as described further below.

The plain text document 1004 may then be provided to a CLU system 1006 having an NLU engine. The CLU system may annotate the plain text document 1004 in any suitable manner. For example, in some embodiments the CLU system 1006 may derive applicable medical codes from the plain text document. The medical codes may be any of those types described herein (e.g., medical diagnosis codes, medical procedure or treatment codes, other medical billing codes, etc.) or any other suitable code types. Also, annotations other than codes may alternatively or additionally be generated in some embodiments.

The CLU system 1006 may generate or provide (as an output) a tokenized document and a document containing annotations. The tokenized document may be, in some embodiments, a tokenized XHTML document. Such a document may be generated by tokenizing words and phrases in the document. Character offsets of the tokens may be returned by the CLU system 1006. The document containing annotations may be any suitable document, a non-limiting example of which is the illustrated application XML 1008. Thus, it should be appreciated that the annotations may be maintained in a separate document from the tokenized document.

Evidence, tied to codes (e.g., medical codes of the types described above) may also be returned by the CLU system 1006. The evidence may represent support for the generated codes, such as text in the document identified as supporting the generation of a particular code. Thus, evidence may be in the form of one or more portions of a document being annotated. The evidence, or location (document position, offset) information for the evidence, may be identified in the document containing the annotations (e.g., in the application XML 1008).

The tokenized XHTML document and application XML 1008 may be used to present an annotated XHTML document 1010. That is, the annotations from the application XML 1008 may be applied to the tokenized XHTML document output by the CLU system. In some embodiments, the annotations are applied using an application viewer which presents the annotated document to a user. The annotated XHTML document 1010 therefore represents a richly formatted document including the annotations from CLU system 1006. In some embodiments, the presented annotated richly formatted document is transient in that there may be no document maintained by the system which includes the annotations in a richly formatted document. Rather, in such non-limiting embodiments, the annotations may be applied only in the transient document presented to the user (e.g., via a browser or other viewing application).

In some embodiments, the annotations are applied to the tokenized XHTML output by the CLU system by suitable restructuring of the tokenized XHTML document. For example, the nodes (e.g., the leaf nodes) in the XHTMl document 1002 may be restructured to reflect (or capture) tokens from the CLU system 1006 and the token offsets generated by the CLU system 1006 may be mapped back to nodes of the XHTML document as individual span tags that are assigned (unique) identifiers. Other manners of generating the annotated XHTML document are also possible.

By rendering the XHTML document 1010 (e.g., using any suitable rendering device with a suitable user interface such as or similar to user interface 110), a user may view an annotated version of the medical document with rich formatting. For example, background styles of the tokens that are part of an annotation generated by the CLU system 1006 may be changed to indicate that the CLU system 1006 considers such tokens to represent evidence for the annotations. In this manner, formatting representing evidence from the CLU system 1006 may be overlaid on the original rich formatting of the XHTML document 1002. By retaining the formatting of the medical document, the user may more easily understand the basis for certain annotations and therefore may be able to more easily evaluate and/or correct the annotations than if the annotations were presented in a plain text version.

Any suitable system may be used to implement the document flow of FIG. 10. For example, a CLU system of the types described herein may be used. In some embodiments, the document flow may be implemented as part of a CAC system.

Figure 11:
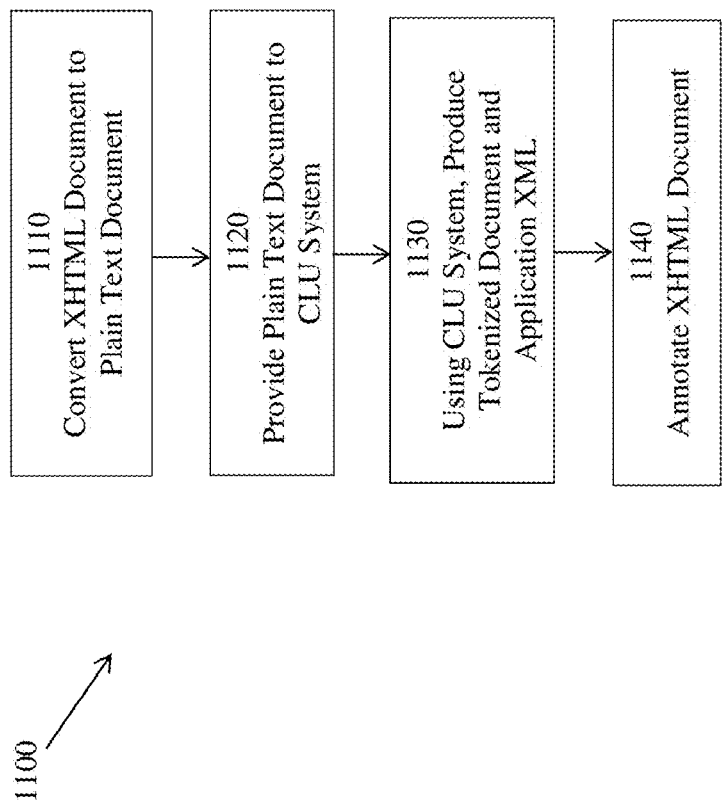
FIG. 11 illustrates a method which may be used to generate an annotated document in connection with the document flow of FIG. 10, according to a non-limiting embodiment of the present application.

FIG. 11 illustrates a method which may be used to generate an annotated document in connection with the document flow of FIG. 10, according to a non-limiting embodiment of the present application. The method 1100 may begin at stage 1110 by converting an XHTML document structured to represent (or have) rich formatting into a plain text document. The XHTML document may be XHTML document 1002 described in connection with FIG. 10 and thus may represent a medical document in some embodiments, although other types of documents may alternatively be used. The plain text document may be plain text document 1004 and may be generated in the manner previously described in connection with FIG. 10 (e.g., by extracting and stringing together text nodes from the XHTML document) or in any other suitable manner.

At stage 1120, the plain text document may be provided to a CLU system (e.g., CLU system 1006 in FIG. 10). The CLU system may tokenize and annotate the plain text document, thus producing, at stage 1130 of the method 1100, a tokenized document (e.g., a tokenized XHTML document) and a document containing annotations (e.g., an application XML) of the types described in connection with FIG. 10.

At stage 1140, the tokenized document and application XML may be used to annotate the XHTML document. For example, as described in connection with FIG. 10, the nodes in the XHTML document may be restructured based on the tokenization of the plain text document by the CLU system in a manner that reflects the tokens. The background styles of the XHTML document may be changed for tokens associated with annotations of the plain text document by the CLU system, thus providing evidence to the XHTML document. The annotation of the XHTML document may be performed as part of a step of rendering the document for a user, for example using an application viewer (e.g., a CAC application viewing program). Thus, the method may provide the user with an annotated version of the original document (e.g., an original medical record) in rich formatting.

Figure 12A:
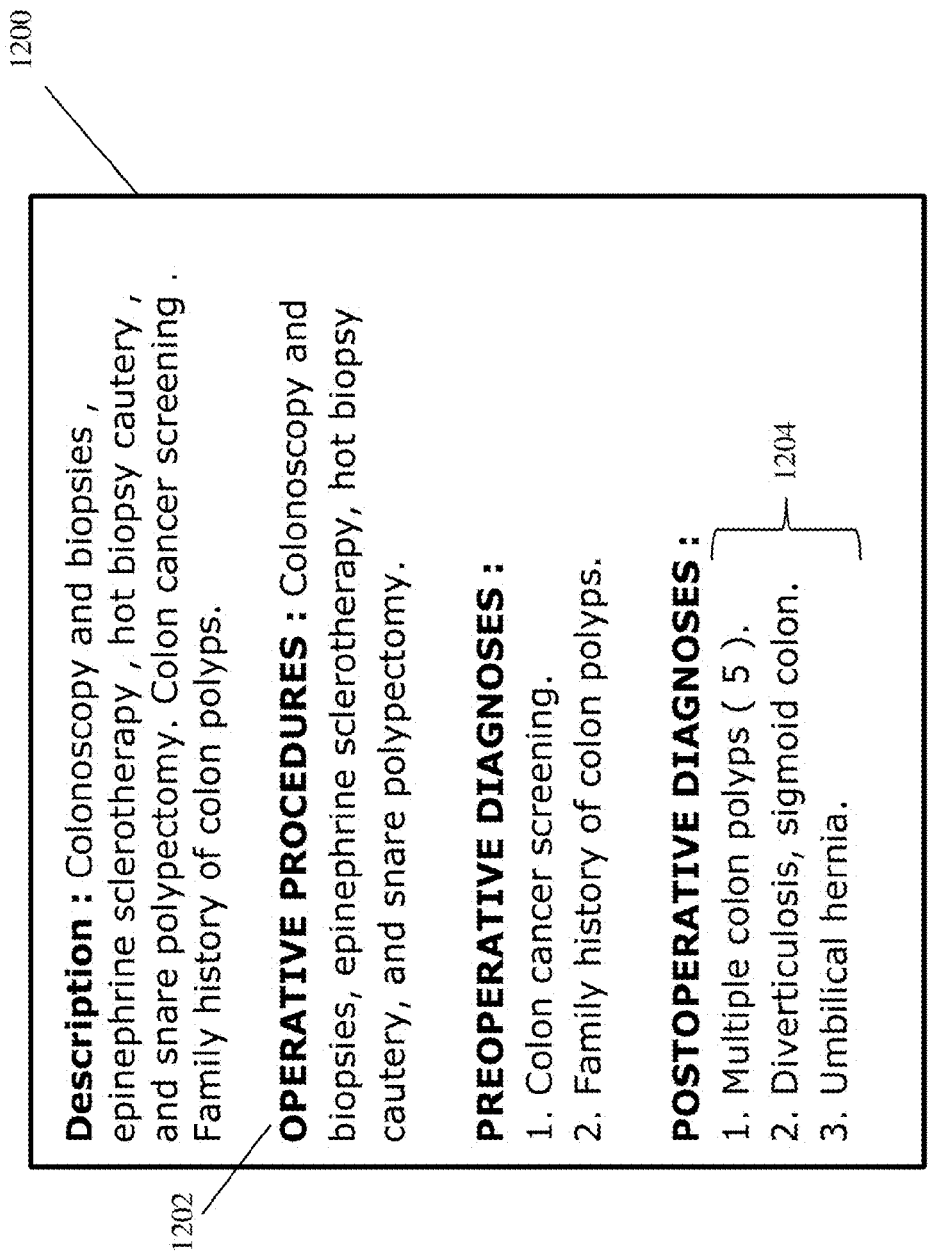
Figure 12C:
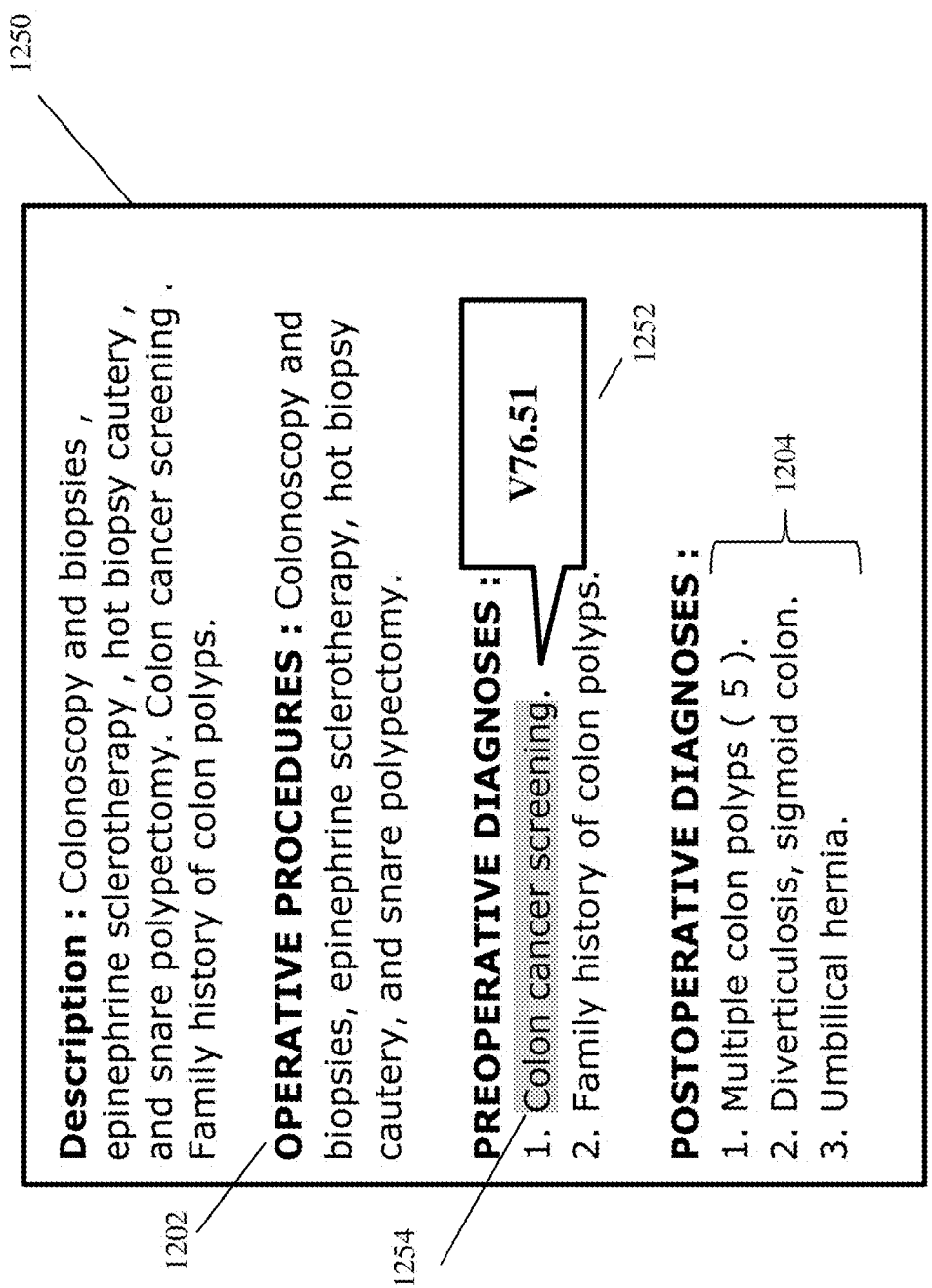

FIGS. 12A-12C illustrate non-limiting examples of documents which may be used or associated with the document flow of FIG. 10 and/or the method of FIG. 11. FIG. 12A illustrates a non-limiting example of a tokenized XHTML document 1200 which may be output by a CLU system as described above in connection with FIG. 10. The tokenized XHTML has rich formatting, including headings 1202 which, in this non-limiting example, include bold text. It can be seen from FIG. 12A that the text of the tokenized XHTML document 1200 is arranged into sections delineated by the headings 1202. Also, content arranged in bullet lists (e.g., bullet list 1204) is included. The tokenized XHTML document 1200 may reflect (substantially or entirely) the formatting of an original clinical document (e.g., rich text document 1001) input to the CLU system, and thus the original rich text document is not shown separately.

FIG. 12B is a non-limiting example of a document 1210 including annotations output by a CLU system. In this non-limiting example, the annotations relate to ICD9 codes as indicated by the "coding system type" heading 1212, and thus the illustrated document represents an example of an output from a CAC system. The document 1210 includes a document ID 1214, as well as annotation IDs 1216 identifying distinct annotations. The annotations are specific to tokens 1218, differentiated by token offsets 1220 as previously described in connection with FIG. 10.

The document 1210 also includes code ID 1222 representing a code annotation for the document, which in this case is a code (V76.51) corresponding to an ICD9 code. It should be appreciated that other codes and other annotations could alternatively be used.

The document 1210 represents a partial document of annotations, and in practice such a document may be larger or smaller than that shown.

FIG. 12C illustrates an example of a rendered document 1250 which may be presented to a user (e.g., by a CAC application viewer or other suitable viewing application) and which represents annotations displayed with rich formatting. In this sense, the document 1250 may represent the annotated XHTML document 1010 of FIG. 10, as a non-limiting example.

As shown, the document 1250 is substantially the same as document 1200 of FIG. 12A except for the addition of an annotated code 1252 (code V76.51) and highlighting 1254. The highlighting 1254 may serve as evidence supporting the annotation 1252, so that a user (e.g., a human reviewer) may assess the accuracy of the annotation 1252. It should be appreciated that presentation of the annotation in the form shown, with rich formatting, may aid review of the annotation compared to if the annotation had been presented as part of a plain text document.

Figure 13:
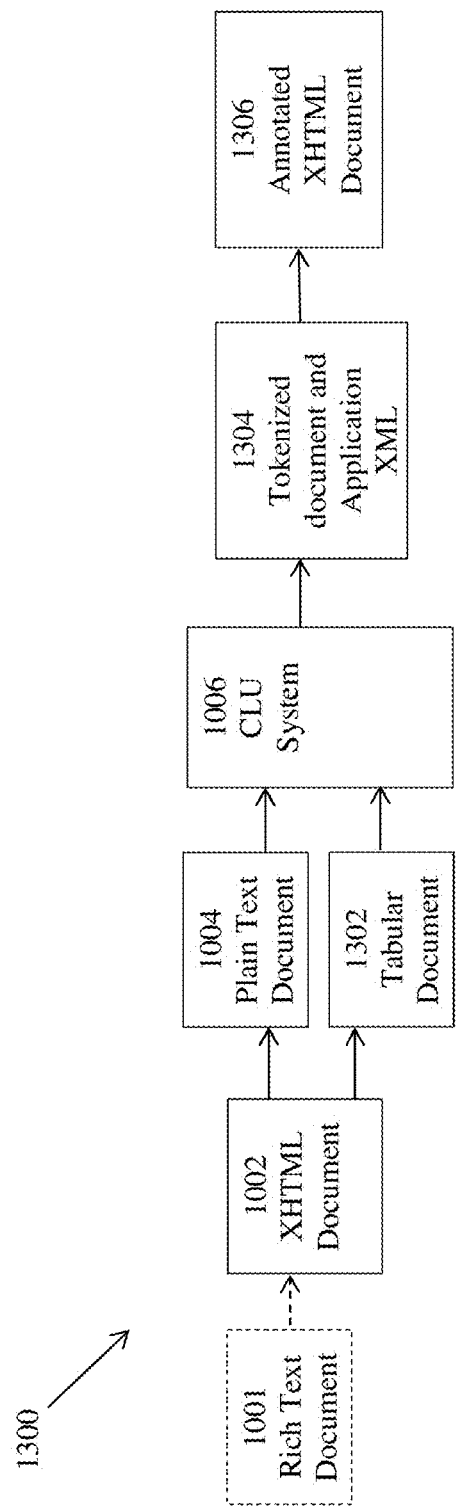
FIG. 13 illustrates a document flow for generating an annotated document in which tabular content is included, according to a non-limiting embodiment of the present application.

FIG. 13 illustrates an alternative document flow to that of FIG. 10 in which tabular content is included, according to a non-limiting embodiment of the present application. As described previously in connection with FIG. 10, a document to be annotated may include rich formatting. In some embodiments, the document may include tabular data. It may be desirable to retain the tabular data and formatting when presenting the user with an annotated version of the document. FIG. 13 illustrates a document flow which may be used when tabular content is involved.

As shown, the document flow 1300 retains elements of the document flow 1000, which are not described again in detail here. In addition to the plain text document 1004, a tabular document 1302 is generated from the XHTML document 1002 by extracting any tables in the XHTML document 1002. Both the plain text document 1004 and the tabular document 1302 are provided to the CLU system 1006. As with the plain text document 1004, the CLU system annotates the tabular document 1302.

The CLU system 1006 generates a tokenized document and application XML 1304 similar to that described above in connection with FIG. 10, the difference being that the tabular content is included in the tokenized document and application XML 1304. The tokenized document and application XML 1304 is then used to annotate the XHTML document 1002 in the manner previously described in connection with FIG. 10, thus resulting in an annotated XHTML document 1306. As with the annotated XHTML document 1010, the annotated XHTML document 1306 may be a document presented to a user (e.g., via a suitable viewing application) and may, in some embodiments, be transient. That is, in some embodiments, the presented annotated richly formatted document is not maintained by the system.

Figure 14:
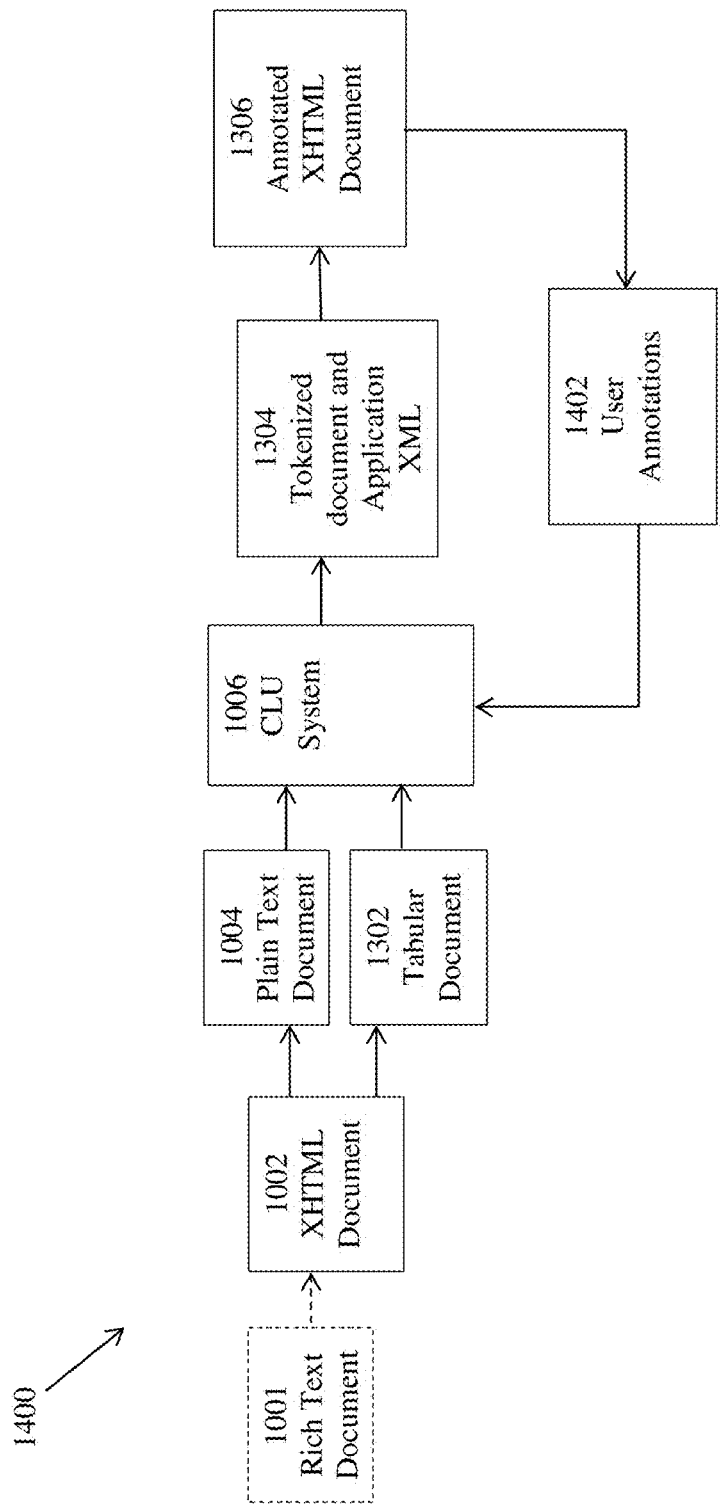
FIG. 14 illustrates a scheme for developing and providing training data for a clinical language understanding (CLU) system, according to a non-limiting embodiment of the present application.

FIG. 14 illustrates a scheme for developing and providing training data for a CLU system, according to a non-limiting embodiment of the present application. The scheme expands upon the document flows of FIGS. 10 and 13 and the associated methods. Those elements which FIGS. 10 and 13 have in common with FIG. 14 are not described again in detail here.

As previously described in connection with FIG. 13, an annotated XHTML document 1306 may be generated. A user may be able to view the document when suitably rendered, for example in a suitable user interface. A non-limiting example may be the rendered document 1250 of FIG. 12C. The user may be a medical coding specialist, a medical reviewer, or any other type of user who may use such documents. It may be desirable, in some situations, for the user to edit (or annotate) the annotations of the XHTML document 1306. For example, the annotated XHTML document 1306 may include annotations suggested by the CLU system 1006 (e.g., annotation 1252 shown in FIG. 12C). The user may disagree with one or more of the suggested annotations, may wish to add one or more annotations not suggested by the CLU system 1006, or may wish to further annotate the annotated XHTML document for any other reason.

Aspects of the present application allow a user to view the annotations of an annotated medical document in rich formatting, and/or to annotate the document in rich formatting. For example, the user viewing the annotated XHTML document 1306 may generate user annotations 1402 of the document. The user annotations 1402 may include corrected or additional medical codes or other forms of annotations. The user annotations may also include supporting evidence, which the user may generate by, for example, selecting appropriate portions of the XHTML document. Such selection may be performed by highlighting the appropriate portions, underlining the appropriate portions, selecting one or more items from a menu (e.g., a drop-down menu presented on the user interface), or in any other suitable manner. As a non-limiting example, a user viewing the document 1250 may wish to add a code not suggested by the CLU system. To do so, the user may highlight text of the document 1250 and then be presented with an input box on a GUI in which to type the code to be added corresponding to the highlighted text. Other forms of user annotations are also possible, as this is a non-limiting example.

The user annotations 1402 may be provided back to the CLU system 1006 as shown in FIG. 14, and the CLU system 1006 may be trained (or re-trained, as the case may be) accordingly. For example, the user may select text (contiguous or non-contiguous) in the annotated XHTML document 1306 and associate the selected text with a code (e.g., a medical diagnosis code or medical procedure code). Tokens associated with the selected text may be mapped from the span identifiers back to the offsets in the plain text document, described previously herein. This feedback may be used for purposes of training the CLU system 1006.

The aspects of the present application may provide one or more benefits, some of which have been previously described. Now described are some non-limiting examples of such benefits. It should be appreciated that not all aspects and embodiments necessarily provide all of the benefits now described. Further, it should be appreciated that aspects of the present application may provide additional benefits to those now described.

As has been described, aspects of the present application provide for presentation of annotated medical or other clinical documents in rich formatting. The rich formatting may facilitate review and analysis of the annotated documents, for example by providing the reviewer (e.g., a human user) with valuable formatting information. Accordingly, review and analysis of annotations may be made more accurate. Also, entry of new annotations or corrections from the user may be simplified and made more accurate.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present invention comprises at least one computer-readable storage medium (i.e., a tangible, non-transitory computer-readable medium, such as a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs any of the above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present invention.

The phraseology and terminology used herein is for the purpose of description and should not be regarded as limiting. The use of "including," "comprising," "having," "containing", "involving", and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements from each other.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A method comprising:
    converting a medical document, having textual content and rich formatting, into a first XHTML document that retains the textual content and the rich formatting of the medical document, the first XHTML document including a first text string in rich formatting;
    generating from the first XHTML document a plain text document that retains the textual content and not the rich formatting of the first XHTML document, wherein generating the plain text document comprises extracting text nodes from the first XHTML document and forming the plain text document from the extracted text nodes, the plain text document including the first text string in plain text without rich formatting;
    generating one or more annotations of the plain text document by applying a natural language understanding (NLU) engine implemented on a processor to the plain text document, the one or more annotations including a first annotation linked to the first text string in the plain text document without rich formatting; and
    displaying an annotated XHTML document created by applying the one or more annotations of the plain text document to a tokenized XHTML document including the textual content and the rich formatting of the medical document, the tokenized XHTML document including the first text string in rich formatting, wherein displaying the annotated XHTML document comprises displaying the first annotation linked to the first text string in rich formatting in the tokenized XHTML document.

2. The method of claim 1, wherein applying the one or more annotations of the plain text document to the tokenized XHTML document is performed as part of a rendering process in which the tokenized XHTML document is rendered in a user interface.

3. The method of claim 1, further comprising generating the tokenized XHTML document by tokenizing the first XHTML document.

4. The method of claim 1, further comprising maintaining the one or more annotations in a document separate from the tokenized XHTML document.

5. The method of claim 1, wherein the one or more annotations comprise a medical code.

6. The method of claim 1, further comprising:
    receiving from a user, via the user interface, a selection of a portion of the annotated XHTML document and an annotation corresponding to the portion; and
    generating tag data mapping the annotation corresponding to the portion to one or more locations in the tokenized XHTML document corresponding to the portion.

7. The method of claim 6, further comprising providing the tag data to the NLU engine and re-training the NLU engine using the tag data and the plain text document.

8. A computer-readable storage medium having instructions that, when executed by a processor, cause performance of a method comprising:
    converting a medical document, having textual content and rich formatting, into a first XHTML document that retains the textual content and the rich formatting of the medical document, the first XHTML document including a first text string in rich formatting;
    generating from the first XHTML document a plain text document that retains the textual content and not the rich formatting of the first XHTML document, wherein generating the plain text document comprises extracting text nodes from the first XHTML document and forming the plain text document from the extracted text nodes, the plain text document including the first text string in plain text without rich formatting;
    generating one or more annotations of the plain text document by applying a natural language understanding (NLU) engine implemented on a processor to the plain text document, the one or more annotations including a first annotation linked to the first text string in the plain text document without rich formatting; and
    displaying an annotated XHTML document created by applying the one or more annotations of the plain text document to a tokenized XHTML document including the textual content and the rich formatting of the medical document, the tokenized XHTML document including the first text string in rich formatting, wherein displaying the annotated XHTML document comprises displaying the first annotation linked to the first text string in rich formatting in the tokenized XHTML document.

9. The computer-readable storage medium of claim 8, wherein applying the one or more annotations of the plain text document to the tokenized XHTML document is performed as part of a rendering process in which the tokenized XHTML document is rendered in a user interface.

10. The computer-readable storage medium of claim 8, wherein the method further comprises generating the tokenized XHTML document by tokenizing the first XHTML document.

11. The computer-readable storage medium of claim 8, wherein the method further comprises maintaining the one or more annotations in a document separate from the tokenized XHTML document.

12. The computer-readable storage medium of claim 8, wherein the one or more annotations comprise a medical code.

13. The computer-readable storage medium of claim 8, wherein the method further comprises:
    receiving from a user, via the user interface, a selection of a portion of the annotated XHTML document and an annotation corresponding to the portion; and
    generating tag data mapping the annotation corresponding to the portion to one or more locations in the tokenized XHTML document corresponding to the portion.

14. The computer-readable storage medium of claim 13, wherein the method further comprises providing the tag data to the NLU engine and re-training the NLU engine using the tag data and the plain text document.

15. A system, comprising:
a processor; and
a memory coupled to the processor and storing computer-readable instructions which, when executed by the processor, cause performance of a method comprising:
converting a medical document, having textual content and rich formatting, into a first XHTML document that retains the textual content and the rich formatting of the medical document, the first XHTML document including a first text string in rich formatting;
generating from the first XHTML document a plain text document that retains the textual content and not the rich formatting of the first XHTML document, wherein generating the plain text document comprises extracting text nodes from the first XHTML document and forming the plain text document from the extracted text nodes, the plain text document including the first text string in plain text without rich formatting;
generating one or more annotations of the plain text document by applying a natural language understanding (NLU) engine implemented on a processor to the plain text document, the one or more annotations including a first annotation linked to the first text string in the plain text document without rich formatting; and
displaying an annotated XHTML document created by applying the one or more annotations of the plain text document to a tokenized XHTML document including the textual content and the rich formatting of the medical document, the tokenized XHTML document including the first text string in rich formatting, wherein displaying the annotated XHTML document comprises displaying the first annotation linked to the first text string in rich formatting in the tokenized XHTML document.

16. The system of claim 15, wherein applying the one or more annotations of the plain text document to the tokenized XHTML document is performed as part of a rendering process in which the tokenized XHTML document is rendered in a user interface.

17. The system of claim 15, wherein the method further comprises generating the tokenized XHTML document by tokenizing the first XHTML document.

18. The system of claim 15, wherein the method further comprises maintaining the one or more annotations in a document separate from the tokenized XHTML document.

19. The system of claim 15, wherein the one or more annotations comprise a medical code.

20. The system of claim 15, wherein the method further comprises:
receiving from a user, via the user interface, a selection of a portion of the annotated XHTML document and an annotation corresponding to the portion; and
generating tag data mapping the annotation corresponding to the portion to one or more locations in the tokenized XHTML document corresponding to the portion.

* * * * *